(12) United States Patent
Bilgicer et al.

(10) Patent No.: US 9,598,460 B2
(45) Date of Patent: Mar. 21, 2017

(54) ANTIBODY PURIFICATION VIA AFFINITY CHROMATOGRAPHY

(75) Inventors: Zihni Basar Bilgicer, Granger, IN (US); Tanyel Kiziltepe Bilgicer, Granger, IN (US); Nathan Joseph Alves, Woodbury, CT (US); Jonathan Darryl Ashley, Olathe, KS (US); Michael William Handlogten, Rochester, MN (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 372 days.

(21) Appl. No.: 13/979,919

(22) PCT Filed: Jan. 18, 2012

(86) PCT No.: PCT/US2012/021704
§ 371 (c)(1),
(2), (4) Date: Jul. 16, 2013

(87) PCT Pub. No.: WO2012/099949
PCT Pub. Date: Jul. 26, 2012

(65) Prior Publication Data
US 2013/0309699 A1 Nov. 21, 2013

Related U.S. Application Data

(60) Provisional application No. 61/461,429, filed on Jan. 18, 2011.

(51) Int. Cl.
| | | |
|---|---|---|
| *C07K 1/14* | (2006.01) | |
| *C07K 1/22* | (2006.01) | |
| *C07K 16/06* | (2006.01) | |
| *A61K 39/395* | (2006.01) | |
| *C07K 16/28* | (2006.01) | |
| *C07K 16/32* | (2006.01) | |

(52) U.S. Cl.
CPC .......... *C07K 1/22* (2013.01); *A61K 39/39591* (2013.01); *C07K 1/14* (2013.01); *C07K 16/065* (2013.01); *C07K 16/2887* (2013.01); *C07K 16/32* (2013.01)

(58) Field of Classification Search
None
See application file for complete search history.

(56) References Cited

U.S. PATENT DOCUMENTS

| | | | |
|---|---|---|---|
| 5,800,991 A * | 9/1998 | Haley et al. | 435/6.11 |
| 5,837,419 A * | 11/1998 | Ushirogouchi et al. | 430/270.1 |
| 2008/0274102 A1 | 11/2008 | Wallach et al. | |
| 2009/0095677 A1 | 4/2009 | Kim et al. | |
| 2009/0117103 A1 | 5/2009 | Devalaraja et al. | |
| 2009/0208418 A1 | 8/2009 | Kohler et al. | |
| 2010/0160605 A1* | 6/2010 | Komiya et al. | 530/344 |
| 2010/0172894 A1 | 7/2010 | Brown et al. | |
| 2011/0319592 A1* | 12/2011 | St. Hilaire et al. | 530/322 |

OTHER PUBLICATIONS

Platis et al. "Affinity chromatogrpahy for the purificaiton of therapeutic proteins from transgenic maize using immobilized histamine" J. Sep Sci, 2008, 31, 636-645.*
Rajagopalan, Krishnan et al., "Novel Unconventional Binding Site in the Variable Region of Immunoglobulins," Proc. Natl. Acad. Sci. USA, 1996, vol. 93, pp. 6019-6024.

* cited by examiner

*Primary Examiner* — Sharon Wen
*Assistant Examiner* — James Rogers
(74) *Attorney, Agent, or Firm* — Husch Blackwell LLP; Denise L. Mayfield

(57) ABSTRACT

Embodiments herein provide methods of purifying monoclonal and polyclonal antibodies (e.g., immunoglobulins) from biological fluids, such as cell lysates, cell supernatant and ascites fluids, using small molecule affinity chromatography. Various embodiments disclose a class of small molecules that selectively bind a nucleotide binding site that is inherent to all immunoglobulins, and in various embodiments, methods are disclosed that use one of these small molecules as a capture molecule in small molecule affinity chromatography. In some embodiments, the small molecule may be an indole, and in particular embodiments, the small molecule may be indole-3-butyric acid.

18 Claims, 17 Drawing Sheets

Rituximab – RCSB PDB ID: 2OSL

*Light Chain* (SEQ. ID. NO: 1)

| | |
|---|---|
| 1 | QIVLSQSPAI LSASPGEKVT MTCRASSSVS YIHWFQQKPG SSPKPWIYAT |
| 51 | SNLASGVPVR FSGSGSGTSY SLTISRVEAE DAATYYCQQW TSNPPTFGGG |
| 101 | TKLEIKRTVA APSVFIFPPS DEQLKSGTAS VVCLLNNFYP REAKVQWKVD |
| 151 | NALQSGNSQE SVTEQDSKDS TYSLSSTLTL SKADYEKHKV YACEVTHQGL |
| 201 | SSPVTKSFNR GEC |

*Heavy Chain* (SEQ. ID. NO: 2)

| | |
|---|---|
| 1 | QVQLQQPGAE LVKPGASVKM SCKASGYTFT SYNMHWVKQT PGRGLEWIGA |
| 51 | IYPGNGDTSY NQKFKGKATL TADKSSSTAY MQLSSLTSED SAVYYCARST |
| 101 | YYGGDWYFNV WGAGTTVTVS AASTKGPSVF PLAPSSKSTS GGTAALGCLV |
| 151 | KDYFPEPVTV SWNSGALTSG VHTFPAVLQS SGLYSLSSVV TVPSSSLGTQ |
| 201 | TYICNVNHKP SNTKVDKKVE PKSC |

Figure 2C

Herceptin – RCSB PDB ID: 1N8Z

*Light Chain* (SEQ. ID. NO: 3)

| | |
|---|---|
| 1 | DIQMTQSPSS LSASVGDRVT ITCRASQDVN TAVAWYQQKP GKAPKLLIYS |
| 51 | ASFLYSGVPS RFSGSRSGTD FTLTISSLQP EDFATYYCQQ HYTTPPTFGQ |
| 101 | GTKVEIKRTV AAPSVFIFPP SDEQLKSGTA SVVCLLNNFY PREAKVQWKV |
| 151 | DNALQSGNSQ ESVTEQDSKD STYSLSSTLT LSKADYEKHK VYACEVTHQG |
| 201 | LSSPVTKSFN RGEC |

*Heavy Chain* (SEQ. ID. NO: 4)

| | |
|---|---|
| 1 | EVQLVESGGG LVQPGGSLRL SCAASGFNIK DTYIHWVRQA PGKGLEWVAR |
| 51 | IYPTNGYTRY ADSVKGRFTI SADTSKNTAY LQMNSLRAED TAVYYCSRWG |
| 101 | GDGFYAMDYW GQGTLVTVSS ASTKGPSVFP LAPSSKSTSG GTAALGCLVK |
| 151 | DYFPEPVTVS WNSGALTSGV HTFPAVLQSS GLYSLSSVVT VPSSSLGTQT |
| 201 | YICNVNHKPS NTKVDKKVEP |

Figure 2D

| Inject # | Buffer | Volume (µL) | [Rituximab] mg/mL | [BSA] mg/mL | FQ Time (min) | Gradient Time (min) | 280nm Integration | % Recovery |
|---|---|---|---|---|---|---|---|---|
| 1 | PBS pH 7.4 | 20 | 2.5 | 0 | 5 | 10 | 2417.8 | 102.9 |
| 2 | PBS pH 7.4 | 20 | 2.5 | 0 | 5 | 10 | 2261.3 | 96.2 |
| 3 | PBS pH 7.4 | 20 | 2.5 | 0 | 5 | 10 | 2371.6 | 100.9 |
| | | | | | | Average: | 2350.2 ±80.4 | 100.0 ±3.4 |
| 4 | PBS pH 7.4 | 20 | 1.5 | 0 | 5 | 10 | 1403.4 (2339.1) | 99.5 |
| 5 | PBS 0.05% Tween20 | 20 | 2.5 | 0 | 5 | 10 | 2264.6 | 96.4 |
| 6 | PBS pH 7.4 | 20 | 2.5 | 0 | 10 | 10 | 2459.0 | 104.6 |
| 7 | PBS pH 7.4 | 20 | 2.5 | 0 | 15 | 10 | 2269.6 | 96.6 |
| 8 | PBS pH 7.4 | 20 | 2.5 | 0 | 240 | 10 | 2648.6 | 112.7 |
| 9 | PBS pH 7.4 | 20 | 2.5 | 0 | 5 | 20 | 2271.7 | 96.7 |
| 10 | PBS pH 7.4 | 1000 | 0.05 | 0 | 5 | 10 | 2545.7 | 108.3 |
| 11 | PBS pH 7.4 | 20 | 2.5 | 5 | 5 | 10 | 2236.9 | 95.2 |
| 12 | PBS pH 7.4 | 20 | 2.5 | 15 | 5 | 10 | 2247.0 | 95.6 |
| 13 | PBS pH 7.4 | 20 | 2.5 | 25 | 5 | 10 | 2396 | 101.9 |

Figure 4A

ANTIBODY PURIFICATION VIA AFFINITY CHROMATOGRAPHY

CROSS REFERENCE TO RELATED APPLICATIONS

The present application claims priority to U.S. Provisional Patent Application No. 61/461,429, filed Jan. 18, 2011, entitled "ANTIBODY PURIFICATION VIA AFFINITY CHROMATOGRAPHY," the disclosure of which is hereby incorporated by reference in its entirety.

TECHNICAL FIELD

Embodiments herein relate to the field of antibody purification, and, more specifically, to compositions and methods for antibody purification via affinity chromatography.

BACKGROUND

Antibodies are plasma proteins produced by the immune system as a response to foreign substances in the body, and are used for a wide variety of diagnostic, therapeutic, and research applications. For example, antibodies may be used in ELISA assays for detection and diagnosis of analytes and markers, as components of biosensors, as imaging agents, as pharmaceuticals, and in countless other uses. In the last fifteen years, monoclonal antibodies have been developed to be used as therapeutics to treat many human diseases, including various cancers and autoimmune diseases. Due to their high level of specificity and selectivity toward known targets, antibodies produce few nonspecific interactions, which reduce the side effects associated with many treatments.

Typically, antibodies are obtained through the purification of biological fluids, such as plasma, cell lysates, ascites fluid, and in the case of monoclonal antibodies produced in cell culture from hybridoma cells, from cell culture supernatant. Antibody purification may include any of a number of processes, such as ammonium sulfate precipitation, ion-exchange chromatography, hydrophobic interaction chromatography, and affinity chromatography. Existing processes for purifying antibodies involve multiple steps that may have detrimental effects on the specific activity of isolated antibodies. For example, during purification, several processes may result in low yields and defective antibodies, including protein unfolding, misfolding, and aggregation; covalent modification (e.g., oxidation); enzymatic proteolysis; and the "scrambling" of light chains. Procedures for purifying antibodies generally are designed to remove a number of contaminants, such as host cell proteins, DNA, endotoxins, and cell culture media additives. In addition, antibody-derived impurities, such as high-molecular-weight aggregates and proteolytic fragments of immunoglobulin, may also contaminate the desired product.

Affinity chromatography is useful because it allows the possibility of obtaining several fold purification with high recovery in a single step. Protein A and protein G are the most commonly used capture proteins in the purification of human antibodies. However, protein A and protein G have several drawbacks, including their high cost, low stability, and the possibility of contaminating the product through hydrolysis and release of peptide fragments.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 2C illustrates the single letter amino acid sequence for the Fab fragment (light chain (SEQ ID NO: 1) and heavy chain (SEQ ID NO: 2)) of Rituximab (RCSB PDB ID:2OSL; SEQ. ID NO: 1) with the residues that comprise the nucleotide binding site highlighted, in accordance with various embodiments;

FIG. 2D illustrates the single letter amino acid sequence for the Fab fragment (light chain (SEQ ID NO: 3) and heavy chain (SEQ ID NO: 4)) of Herceptin (RCSB PDB ID:1N8Z) with the residues that comprise the nucleotide binding site highlighted, in accordance with various embodiments;

FIG. 4A is a table showing the effects of varying injection volume, antibody amount, elution gradient time, and wash/bind time regarding injected antibody recovery based on absorbance peak integration values, in accordance with various embodiments;

DETAILED DESCRIPTION OF DISCLOSED EMBODIMENTS

Figure 1:
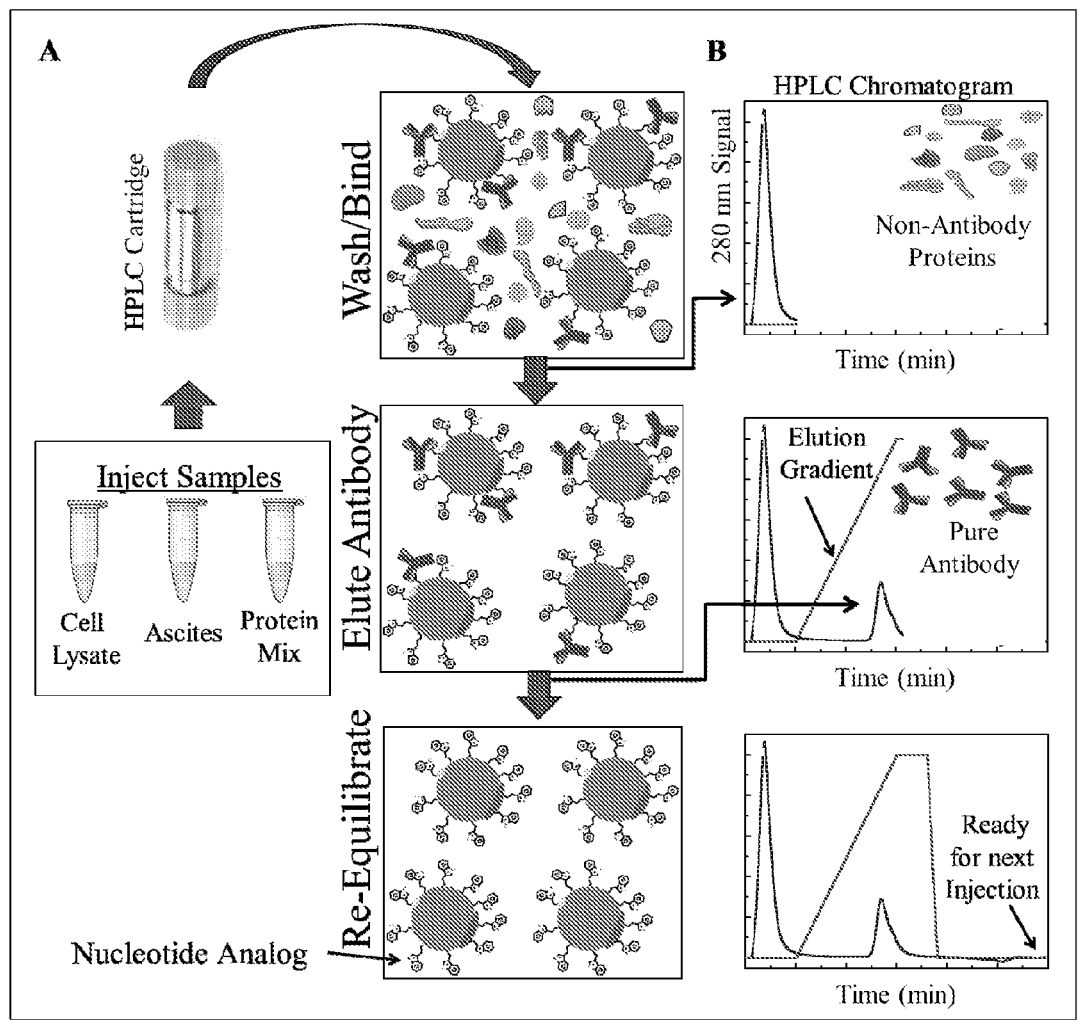
FIG. 1 is a diagram of one example of a purification platform, including chromatogram and gradient information, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide methods of purifying monoclonal and polyclonal antibodies (e.g., immunoglobulins) from biological fluids, such as cell lysates, cell supernatant and ascites fluids, using affinity chromatography. Affinity chromatography is a purification method that uses an immobilized capture molecule (ligand) that selectively binds to a target molecule (such as an antibody) contained in a more complex mixture of contaminating molecules. This method of purification is typically carried out under flowing conditions (e.g., in the mobile phase) in a column packed with a resin (e.g., the immobile phase) that contains the immobilized capture molecule (e.g., the ligand). In various embodiments, the purification process may begin with the introduction of the sample to be purified into the column, and the sample may be dissolved in a buffer that functions as the mobile phase. In various embodiments, this buffer may promote binding of the target molecule to the capture molecule on the resin, while other contaminant molecules are washed away. In various embodiments, once the target molecule has bound to the capture molecule, the flowing mobile phase may be replaced with a buffer that reduces the affinity of the target molecule for its immobilized ligand, which may cause the target molecule to be eluted (e.g., released) from the column.

Typically, in a standard affinity chromatography procedure, the capture molecule is an immobilized protein that binds to a desired protein in a complex mixture. Existing affinity chromatography procedures typically use protein A or protein G as a capture molecule, and the elution of the antibody is achieved by decreasing the pH to 2-3. Although protein A affinity chromatography may yield products with a high degree of purity, it also may introduce a number of additional challenges and routes of contamination. For example, hydrolysis and proteolysis may contaminate the isolated product with cleaved protein A and its truncated derivatives, and leached protein A may adhere to the eluting product. Additionally, the acidic pH of the mobile phase may cause the antibody to unfold and lose activity and/or aggregate non-specifically and precipitate. Furthermore, protein A columns have a short life span, and need to be replaced after a certain number of applications.

Small molecule affinity chromatography differs from standard affinity chromatography in that a small molecule may be immobilized on the resin surface, rather than a protein or peptide. For instance, in various embodiments, instead of a protein ligand, such as protein A or protein G, small molecule affinity chromatography may use a small molecule bound to the immobile phase as a capture molecule during the affinity chromatography process. In various embodiments disclosed herein, the small molecule may be a nucleotide analog, and it may bind to a nucleotide binding site that is present on all antibodies, thus capturing the antibodies. In various embodiments, as further described below, using a small molecule as a capture molecule may greatly increase the column stability, and may also enhance the purity of the recovered target molecule.

The terms "antibody" and "immunoglobulin" are used interchangeably herein, and the basic immunoglobulin structural unit is generally a tetramer. Each tetramer includes two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains. Although the basic antibody structure is a tetramer, as used herein, the terms "antibody" and "immunoglobulin" may refer to a protein that includes at least the variable domain of a heavy chain, and that normally includes at least the variable domains of a heavy chain and a light chain. Antibodies for use with the methods of this disclosure may be monoclonal or polyclonal.

As used herein, the terms "bind specifically" and "specific binding" refer to the ability of a specific binding agent (such as an antibody) to preferentially bind to a target molecular species as compared to other molecular species with which the specific binding agent and target molecular species are admixed. Thus, a specific binding agent may specifically recognize a target molecular species when it can bind specifically to that target.

Thus, disclosed herein are compositions and methods for small molecule-based affinity purification of antibodies, wherein a nucleotide binding site that is inherent to all immunoglobulins is used for capture of the antibody on the immobile phase. Also disclosed is a class of small molecules that selectively bind to this nucleotide binding site, which is located in the variable fragment of antibodies. In some embodiments, the class of small molecules may contain fused aromatic rings, aromatic rings, or indole groups. In various embodiments, small molecules that may be used in the disclosed methods may have a monovalent binding affinity for the nucleotide binding site that is less than about $K_d$=150 μM, and they may have a monomeric molecular weight that is less than about 500 Da.

IgG is a symmetrical bivalent antibody, and therefore it has two nucleotide binding sites. In various embodiments, four residues have been identified that form a nucleotide binding site (two tyrosines or one phenylalanine and one tyrosine on the light chain, and one tyrosine and one tryptophan on the heavy chain), and that are conserved and associated with the nucleotide binding pocket based on >260 immunoglobulin crystal structures available from the RCSB Protein Data Bank. In various embodiments, these four residues may include a phenylalanine or a tyrosine on the light chain, a tyrosine on the light chain, a tyrosine on the heavy chain, and a tryptophan on the heavy chain. Although the exact position in the amino acid sequence of each of these four amino acids may be different in different immunoglobins, in some embodiments they may correspond to phenylalanine 35 and tyrosine 86 in the Rituximab immunoglobulin light chain amino acid sequence shown in SEQ ID NO: 1, and tyrosine 95 and tryptophan 111 in the Rituximab immunoglobulin heavy chain amino acid sequence shown in SEQ ID NO: 2, as illustrated in FIG. 2C. In other embodiments, the four amino acids may correspond to tyrosine 36 and tyrosine 87 of the Herceptin immunoglobulin light chain amino acid sequence shown in SEQ ID NO: 3; and tyrosine 95 and tryptophan 110 of the Herceptin immunoglobulin heavy chain amino acid sequence shown in SEQ ID NO: 4, as illustrated in FIG. 2D. In general, although the small molecules used in the methods disclosed herein will bind to any immunoglobulin, they may be defined as having a monovalent Kd of about 150 μM or less for either:

A. phenylalamine 35 of SEQ. ID NO: 1;
   tyrosine 86 of SEQ. ID NO: 1;
   tyrosine 95 of SEQ. ID NO: 3; and
   tryptophan 111 of SEQ. ID NO: 3; or
B. tyrosine 36 of SEQ. ID. NO: 2;
   tyrosine 87 of SEQ. ID. NO: 2;
   tyrosine 95 of SEQ. ID. NO: 4; and
   tryptophan 110 of SEQ. ID. NO: 4, or both. In various embodiments, such a small molecule will bind not only to the specific sequences defined herein, but also will bind with high affinity to any other immunoglobulin.

In various embodiments, the first amino acid in the nucleotide binding site may be either a tyrosine or a phenylalanine, the difference between a tyrosine and phenylalanine being that a tyrosine is 4-hydroxyphenylalanine, a single hydroxylation in the 4 position of the aromatic ring in phenylalanine. An example of this variation is demonstrated by comparing the positions and amino acid residues that comprise the nucleotide binding pocket in Rituximab (SEQ. ID NOS: 1 and 2) and Herceptin (SEQ. ID. NOS: 3 and 4). While the binding pocket location and amino acid side chain orientation are conserved in the crystal structure overlay, there are slight variations in the position number of the amino acids as a result in differences in the overall backbone sequence variation from antibody to antibody as well as in numbering schemes.

In various embodiments, depending on the small molecule chosen for immobilization, various chemical ligation methods may be employed to produce covalent stable bonds on the resin. In various embodiments, this may allow the system to be reused and regenerated under conditions that would not be possible with standard protein based resin purification systems that employ protein A or its derivatives. As discussed above, in some embodiments, the small molecule may be include an indole. As used herein, the term "indole" refers to an aromatic heterocyclic organic compound having a bicyclic structure that includes a six-membered benzene ring fused to a five-membered nitrogen-containing pyrrole ring. In one specific, non-limiting example, the small molecule may be indole-3-butyric acid:

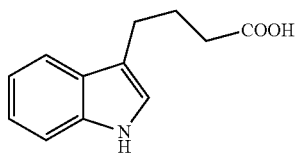 [SMILES: O=C(O)CCCc1c[nH]c2ccccc12]

and the resin and small molecule may be linked via a stable amide bond and therefore may be relatively chemically resistant to harsh organic solvents or denaturants.

Additionally, in existing protein based affinity columns, protein fragments may be leached into the 'purified' antibody as the capture protein misfolds and undergoes hydrolysis. In many examples, this leaching may necessitate the use of serial methods of purification to remove contaminants. By contrast, the methods disclosed herein, which make use of a small molecule capture molecule, may eliminate the possibility of protein fragments leaching into the purified antibody product. Thus, in various embodiments, the disclosed small molecule affinity chromatography methods may result in a one step antibody purification method.

Furthermore, in various embodiments, the high cost associated with expressing recombinant proteins such as protein A may be avoided when a small molecule is used as the capture molecule. Additionally, in many examples, the process of immobilizing proteins on a solid support may result in large amounts of inactive, misfolded, and/or misoriented capture protein on the surface of the solid support, which may cause nonspecific interactions and reduced column capacity. By contrast, in various embodiments, the use of a small molecule in place of a protein may eliminate these problems, while greatly reducing the overall cost associated with purification. In various embodiments, implementation of the disclosed methods (in place of existing methods) may also result in the reduction of consumables associated with pharmaceutical antibody purification, and therefore may reduce waste and increase production efficiency.

Thus, disclosed in various embodiments are small molecule-based affinity chromatography methods that may tolerate the use of harsh coupling methods to immobilize the capture molecule on the resin, that may produce a stable bond between the column packing (e.g., resin) and the small molecule, that may retain maximal binding capacity for the column, and that may optimize the purity of the eluted antibody. In various embodiments, the disclosed methods also may enable the use of harsh solvents to regenerate the column when necessary, they may eliminate column fouling due to denaturing, they may eliminate the need for expensive recombinant proteins, they may increase the number of cycles of purification for which a given column may be used, and they may provide a one column purification platform for any antibody containing the conserved nucleotide binding site.

In various embodiments, the disclosed methods may be used with a liquid chromatography system, and in other embodiments, the disclosed methods also may be used as a stand-alone purification method. For example, FIG. 1 illustrates a diagram of one example of a purification platform, including chromatogram and gradient information, in accordance with various embodiments. In various embodiments, the disclosed methods may be used for any scale of antibody production and purification, from individual small scale laboratory hybridoma expression to industrial grade antibody purification, for example for pharmaceutical antibody production. In various embodiments, the disclosed methods provide a single step purification method that may start with cell lysate, cell supernatant or ascites fluid, and that may produce purified antibody in protein-free elution buffer that, in some examples, may contain only sodium chloride. In various embodiments, this purification technique may also be used without packing a column by conducting the separation as a slurry, and incubating the contaminated antibody in solution with the functionalized small-molecule resin. In this embodiment, a batch type purification system may be implemented, followed by gravity filtration and fraction collection upon elution of the purified antibody.

In some embodiments, even chemical species that may impact indole binding to the nucleotide binding site, such as trisodium citrate and polysorbate 80, may not need to be removed from the sample prior to purification. For example, in some embodiments, due to the high small molecule surface density on the resin and the symmetry in the immunoglobulin, multiple interaction sites are present that may reduce the antibody off-rate from the resin surface. In some embodiments, the increased overall affinity of the antibody to the small molecule may be attributed to a multivalent binding interaction that has a much higher avidity. In some embodiments, multivalent binding enhancements may decrease the apparent $K_d$ value by orders of magnitude, and thus may produce a much tighter binding system. Thus, in various embodiments, contaminants that can only bind monovalently to the nucleotide binding site may be displaced by the small molecules on the resin surface, which may eliminate the need for their pre-purification removal. Thus, no preprocessing or post processing steps may be required in various embodiments.

In addition to small molecule affinity chromatography, the disclosed compositions and methods also may be used for a number of other purposes, as well. For example, in some embodiments, the disclosed compositions and methods enable oriented non-covalent surface immobilization of antibodies, such as in applications for the purification of any small molecule or protein from a mixed protein solution of any kind with the ability to recover both the antibody and the target molecule without modification to either. In various embodiments, this may be accomplished by first flowing an antibody-containing solution through the column described above to immobilize it on the resin surface via the nucleotide binding site. A solution may then be flowed that contains the target molecule specific to the immobilized antibody, thus washing away all other molecules. In various embodiments, increasing the buffer salt concentration may then co-elute the antibody and target molecule.

In other embodiments, prior to eluting the antibody and target molecule, an HRP-modified secondary antibody may be injected into the column that is specific for either the primary antibody or the target molecule. In some embodiments, a fluorescent HRP substrate may then be added to probe for the HRP and quantify the column content. Thus, in some embodiments, the small molecule affinity chromatography platform may be transformed into a reusable column-based ELISA system.

In still other embodiments, the nucleotide binding site may be used for oriented immobilization of antibodies in methods that are not exclusive to resin based affinity chromatography. For instance, in various embodiments, the disclosed methods may be adapted for use with microfluidic devices, immuno-sensor chips, traditional ELISA carried out on plates of various surface composition, or protein microarrays.

The following Examples are provided for illustration only, and are not intended to limit the scope of the disclosure.

EXAMPLES

Example 1

Screening for Small Molecule Capture Molecules

Figure 2A:
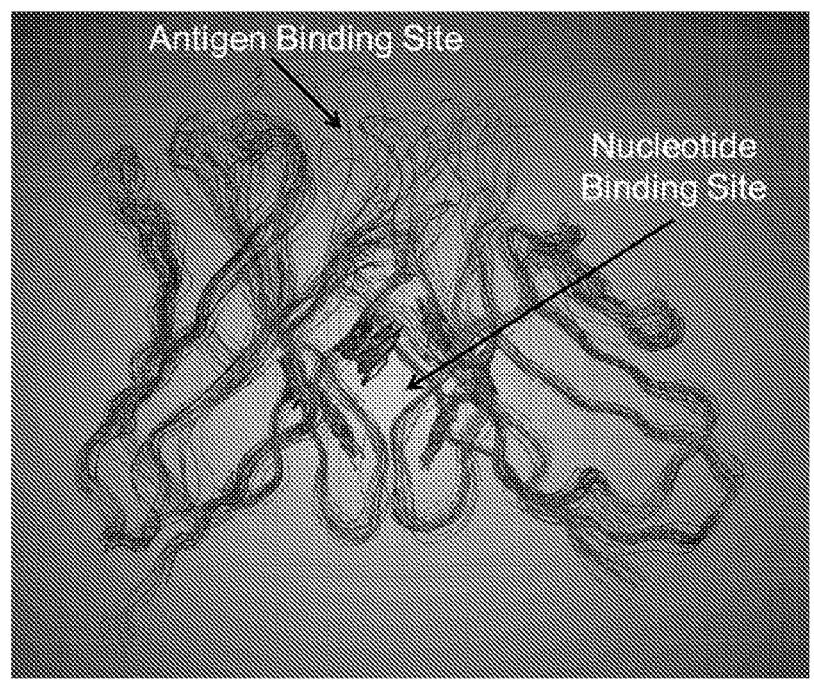
FIG. 2A illustrates a backbone alignment of 18 different IgG, IgM and IgE antibody crystal structures with the residue side chains of the nucleotide binding pocket highlighted, in accordance with various embodiments.

This Example illustrates the methods that were used to identify multiple candidate small molecules that bind to the conserved nucleotide site. As illustrated in FIG. 2A, a backbone alignment of 18 different IgG, IgM, and IgE antibody crystal structures was constructed, and is illustrated with the residue side chains of the nucleotide binding pocket highlighted, in accordance with various embodiments. In this example, the invariability of the side chain configurations demonstrates that the nucleotide binding pocket is conserved through these various antibody isotypes, as well as across a number of different species. In this specific, non-limiting example, using least-squares RMSD crystal structure overlay of various immunoglobulin isotypes from different species visually identifies that the residues associated with the nucleotide binding site are highly conserved in all cases.

In accordance with various embodiments, an in silico screening of ligands was carried out to select for small molecules having high binding affinity for the conserved site. In various embodiments, these small molecules may then be used to bind to any antibody containing this conserved site to extract it from a diverse mixture of proteins, independent of the antibodies' antigen specificity. Of the small molecules initially screened in the database, indole-3-butyric acid had the best docking score. In various embodiments, this small molecule may not need to maintain a native conformation to bind its target because it has nearly no possible structural variation.

Figure 2B:
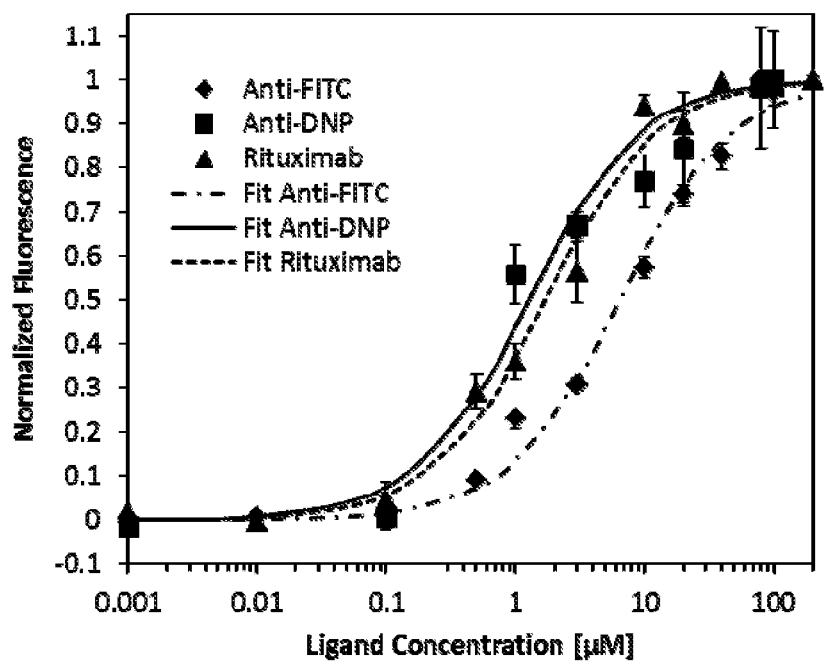
FIG. 2B illustrates the results from a sandwich enzyme-linked immunosorbent assay (ELISA) that was used to determine the binding constant of indole-3 butyric acid for the nucleotide binding site in three different antibodies: Mouse Anti-FITC, Rat Anti-DNP, Human/Mouse Chimeric Rituximab, in accordance with various embodiments.

An enzyme linked immunosorbent assay (ELISA) experiment was conducted to establish the binding affinity of the indole-3-butyric acid for the nucleotide binding site, and to verify that binding this domain does not impact the ability of the antibody to bind to its antigen. FIG. 2B illustrates a sandwich ELISA, in accordance with various embodiments;

In this example, the antigen specific to each antibody was immobilized on a high binding ELISA plate. The primary antibody was then added to bind its antigen, and an increasing concentration of a biotin-linked indole-3 butyric acid molecule was added to each well. HRP-streptavidin was used to bind the biotin, and a fluorescent substrate was used to quantify the amount of indole-3-butyric acid that was present on the surface. Normalizing the fluorescent intensity and fitting the data resulted in the following binding affinities: mouse anti-FITC $K_d$=6.41 µM, rat anti-DNP $K_d$=1.27 µM, chimeric human/mouse Rituximab™ $K_d$=1.7 µM.

Thus, the monovalent $K_d$ values for the indole binding to the nucleotide binding site of three different antibodies ranged between 1-7 µM, showing a 7- to 50-fold enhancement in binding affinity over adenine. The three selected antibodies were chosen as representative examples of different antigen specificity and different host species, and include a currently used pharmaceutical antibody to demonstrate how conserved the nucleotide binding site is.

Figure 2E:
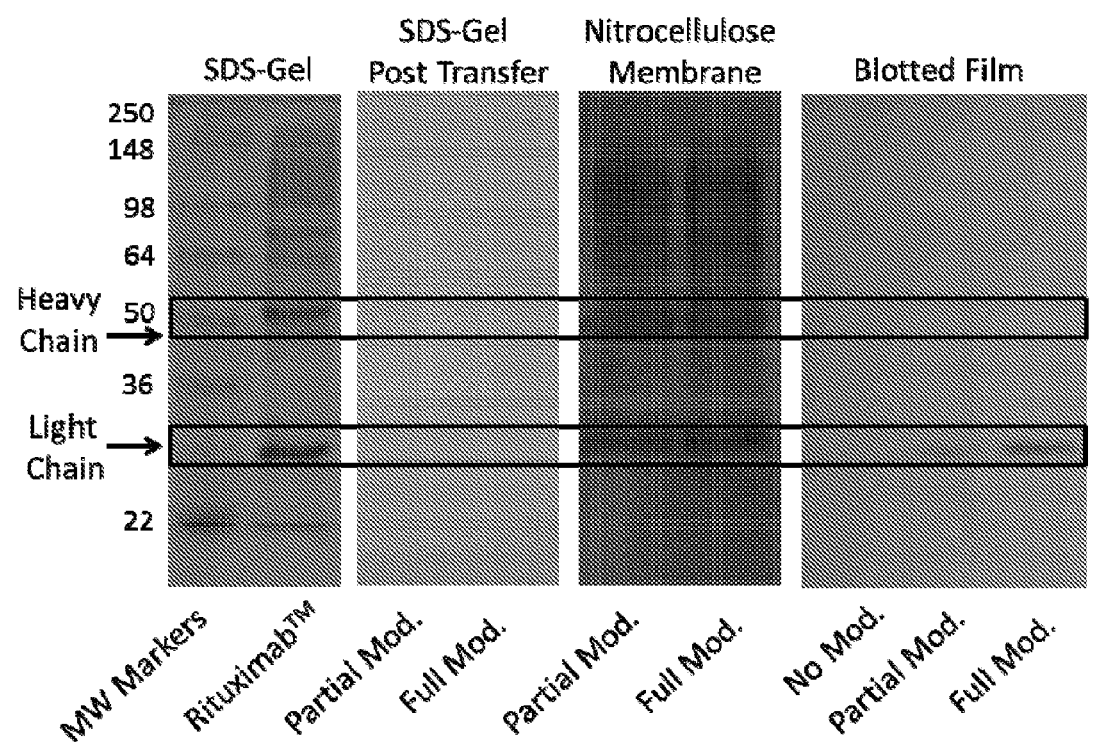
FIG. 2E is a Western blot illustrating the location of the nucleotide binding site on a Fab fragment following a biotinylation procedure that selectively biotinylates the nucleotide binding site, in accordance with various embodiments.

FIG. 2C and FIG. 2D illustrate amino acid sequences of the variable fragment of two pharmaceutical antibodies, Rituximab and Herceptin, with the amino acid residues that form the nucleotide binding pocket highlighted. In accordance with various embodiments, these sequences may illustrate highly conserved relative location of the amino acid backbone, as well as demonstrate the variability between phenylalanine and tyrosine in/near the 35 position of the antibody light chain. In one example shown in FIG. 2E, a Western blot analysis was carried out to verify the specific interaction of indole-3-butyric acid for the nucleotide binding site. In this example, the interaction site between the indole-3-butyric acid and the antibody was determined by incubation of an indole-3-butyric acid-biotin molecule with Rituximab and implementing a selective crosslinking method. Running an SDS-PAGE gel under reducing conditions separated the heavy and light chains of the antibody, and after transfer of the proteins to a nitrocellulose membrane, a strep-HRP reporter protein was used to bind the biotin molecule and determine the insertion location. As indicated in FIG. 2E, the indole-3-butyric acid-biotin molecule was selectively bound to the antibody light chain, signifying that the indole-3-butyric acid antibody interaction is isolated to the Fab fragment where the nucleotide binding pocket is located.

Figure 3:
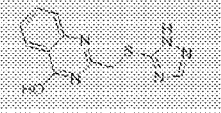
FIG. 3 illustrates the top ten scoring small molecules for binding to the nucleotide binding site, with the highest score at the top, based on Gauss3 (second column) and Gauss2 (fourth column) scoring methods for docking in the nucleotide binding site; in accordance with various embodiments.

While indole-3-butyric acid shows a relatively high binding affinity for the nucleotide binding site, it is not the only small molecule that may be used to carry out affinity purification via this conserved site on the antibody. Further screening of approximately 30 million small molecules in the Zinc database resulted in a rank list of possible molecules similar to indole-3-butyric acid that may serve as alternate nucleotide binding site binders. The top five thousand of these molecules were then docked, as an in silico screening method, into the nucleotide binding site and scored using Open Eye to produce a rank list of the top scoring small molecules. FIG. 3 illustrates the top ten scoring small molecules, with the highest score at the top, based on Gauss3 (second column) and Gauss2 (fourth column) scoring methods for docking in the nucleotide binding site; in accordance with various embodiments.

Example 2

Resin Selection

This Example describes the selection of an appropriate resin for the successful implementation of the disclosed methods of antibody purification. In various embodiments, any of a number of commercially available resins may have appropriate characteristics and may be used. In general, in various embodiments, a suitable small molecule affinity purification resin may have limited swelling in high salt or low pH aqueous buffers, it may be able to withstand nominal pressure drops, it may have a monodisperse pore size and/or a spherical resin diameter, it may have a chemically resistant polymer backbone, it may have limited nonspecific protein adsorption, and/or it may have a highly functionalized surface for ligation. Specific, non-limiting examples of suitable small molecule affinity purification polymer resins include Sepharose™, Fractogel™, CIMGEL™, and Toyo-Pearl™.

In the specific Examples described below, the ToyoPearl™ AF-Amino 650 M resin from Tosoh Biosciences was used. This resin has a methacrylic polymer backbone with hydroxylated aliphatic chains for reduced nonspecific protein adsorption. It is also functionalized with primary amines for acid containing molecule activation and ligation to the resin via amide bond formation.

Example 3

Small Molecule Coupling Methods

This Example describes methods for coupling the small molecule to the resin surface. In various embodiments, any of a variety of synthetic techniques may be used to couple a carboxylic acid-containing small molecule to the primary amines on the resin surface to form a stable amide bond. In one specific, non-limiting example, aqueous phase coupling via 1-Ethyl-3-(3-dimethylaminopropyl)carbodiimide (EDC) activation of the indole-3-butyric acid may be used.

Briefly, the resin was washed with water, with 0.5 M NaCl, and then again with water. Based on amine loading on the resin and the amount of resin being coupled, two molar equivalents of the acid-containing small molecule and two equivalents of EDC were measured out in separate vials. A ratio of 3:1 water:resin was added to the small molecule vial, and 5 molar equivalents of N,N-Diisopropylethylamine (DIEA) were added to the solution to increase small molecule solubility and deprotonate the amines on the resin to increase coupling efficiency. The small molecule and DIEA mixture was then added to the resin.

Next, the EDC was dissolved in water and added to the synthesis vessel, and the resulting solution was agitated for three hours at room temperature (without the use of a stir bar). The resin was then washed in water, and the foregoing steps were repeated. The final reaction pH was adjusted to 5, and coupling was allowed to proceed overnight while the solution was agitated for about 15 hours. The resin was then sequentially washed with water, 0.5 M NaCl, water, 0.1 M sodium hydroxide (NaOH), and finally with water again. In various embodiments, this aqueous reaction may also be conducted using a pH adjusted MES buffer. To acetylate any remaining unreacted amines on the resin, a 0.2 M sodium acetate solution was made of 60% water and 40% acetic anhydride, and the reaction was carried out at room temperature for one hour. The resulting resin was stored as described below.

In other examples, a small molecule may be coupled to the resin surface in an organic solvent. Briefly, the resin was washed sequentially with water, ethanol, and dimethylformamide (DMF), and the resin was then incubated in a synthesis vessel in DMF for 30 minutes (during which time the resin swelled slightly). Based on amine loading on the resin and the amount of resin being coupled, two molar equivalents of acid-containing small molecule and 1.8 molar equivalents of HBTU were measured out in the same vial. A sufficient amount of DMF was added to the ligand to ensure it was fully dissolved and would cover the resin fully in the synthesis vessel. Four molar equivalents of DIEA were then added to the vial, and the mixture was shaken for five minutes to activate the acid and ensure all components were in solution.

The synthesis vessel was then drained of DMF, the activated acid-containing small molecule was added to the synthesis vessel, and coupling proceeded for 2 hours with agitation. The resin was then washed thoroughly with DMF. To acetylate the remaining unreacted amines on the resin, a solution of 60% DMF and 40% acetic anhydride was added to the resin, and the reaction was carried out with shaking at room temperature for one hour. The resin was then sequentially washed in DMF, ethanol, and water, and was stored as described below. In various embodiments, this method provided for a much more efficient, controlled coupling to the resin to vary the small molecule loading ratio when a particular application required a different loading amount.

Example 4

Affinity Chromatography Protocol

This Example illustrates an exemplary set of conditions under which affinity chromatography may be performed using the disclosed small molecules as a capture molecule. In this example, 50 mM sodium phosphate adjusted to pH 7.0 with 1M sodium hydroxide was used as the Wash/Bind and Equilibration Buffer (EQ). The Elution Buffer (ELS) was 50 mM sodium phosphate and 2 M sodium chloride with the pH adjusted to 7.0 with 1M sodium hydroxide, although similar elution profiles were also obtained using an elution buffer of 50 mM sodium phosphate at pH 3.5.

Column Packing

Depending on the application, the resin may be supplied as a slurry to be packed by the end user or as a pre-packed column. If supplied as a slurry, the resin may be washed with water and then ELS buffer prior to packing. The resin is then allowed to settle and equilibrate as a 50% slurry in ELS buffer for at least 30 minutes. In some examples, the column material may be a stainless steel casing with 2 μm frits, which is sufficient in preventing loss of resin without significantly impeding the flow of proteins through the column. In other examples, a number of other column materials may be substituted that exhibit minimal nonspecific protein interactions and that withstand nominal pressure values, and therefore columns for use with the present disclosure are not limited to just stainless steel. In some examples, packing may be carried out by allowing gravity settling of the resin into the column and then attaching the column to a liquid chromatography (LC) system to apply a 5 bar pressure drop across the column while flowing ELS buffer. In various embodiments, the column may then be checked for proper packing of the resin and fritted. At this point the packed column may be ready to be equilibrated and used for antibody purification or stored to be used at a later time.

Storage

Once the column has been sufficiently washed with ELS buffer for 30 minutes to remove any residual protein, the coupled resin may be stored in 20% ethanol and 80% water to prevent microbial growth. In various embodiments, the column may be stored between 4° C. and room temperature indefinitely to be used whenever necessary. In various embodiments, the pre-packed, coupled resin may also be stored as a slurry in the same storage buffer outlined above or as a dried powder.

Use of the Packed Column

In various embodiments, equilibrating a newly packed column or a packed column post storage involves reversing the flow direction and washing with water, ELS buffer, and then again with water. In embodiments, the column is flipped, and ELS buffer is flowed through the column, initially at a low flow rate, and then ramping up to a 5 bar pressure drop across the column. The flow rate needed to produce this pressure drop is maintained for 30 minutes and then reduced to approximately a 1-3 bar pressure drop across the column. The flow is then switched to EQ buffer to allow equilibration of the column for 30 minutes, or until the output absorbance spectrum stabilizes. In various embodiments, this process will repack the resin, making it ready for antibody purification. In various embodiments, column operating pressure should be approximately a 1-3 bar pressure drop across the column, and will increase slightly as the salt content in the column increases throughout the injection cycle.

Solvent Gradient for Antibody Elution

In one specific, non-limiting example, a C-1000 Guard Column may be used that has the dimensions of 1 cm×1 cm (785 µL volume), and stainless steel LC tubing may be used that has a 0.17 mm ID (minimum length). A flow rate of 0.5 mL/min (1-3 bar column pressure drop) may be used, with the following exemplary solvent gradient:

0-5 minutes: hold 100% EQ (wash/bind)
5-15 minutes: linear gradient to 100% ELS (elution gradient)
15-18 minutes: hold 100% ELS (clean)
18-19 minutes: linear gradient to 100% EQ
19-30 minutes: hold 100% EQ (re-equilibrate column)

Injection

In various embodiments, the column specifications outlined above may provide for the efficient capture of 0.25 mg of antibody per injection with an injection volume of between 10 µL and 1000 µL. In various embodiments, the initial non-antibody protein content of the sample may be as high as 25 mg/ml, with an overall salt concentration below 150 mM (PBS) at a relatively neutral pH. In some examples, protein and injection salt concentrations above these values may result in reduced antibody capture efficiency, and therefore the sample may be diluted in EQ buffer to reduce the initial salt and protein concentrations if needed.

Example 5

Purification of an Exemplary Antibody

This Example demonstrates the purification of Rituximab™, a chimeric anti-CD2O pharmaceutical antibody produced by Genentech, using a ToyoPearl™ resin with indole-3-butyric acid coupled via the EDC coupling method outlined above, with no further acetylation to any remaining amines. Several parameters of the protocol were varied in order to demonstrate the efficacy of the system, including injection concentrations and volumes, the wash/bind time, the elution gradient, antibody/protein combinations, and sample injection buffer.

Because the ToyoPearl™ resin is typically used for protein size exclusion separations, it was demonstrated that the antibody retention on the column is not a size exclusion phenomenon associated purely with the resin. Thus, the EQ wash/bind time was varied in order to visualize a change in the antibody elution time. If the antibody retention on the column is not a size exclusion phenomenon, then modifying the initial wash/bind time while keeping the rest of the gradient the same would result in a direct increase or decrease in the antibody elution time identical to the wash/bind time modification. However, if the antibody elution time were purely correlated to a size exclusion effect associated with the resin pore size and particle diameter (e.g., an exclusion limit of 5,000,000 Da with pore sizes of 100 nm) then the elution time would not be directly correlated to the wash/bind time modification.

Figure 4B:
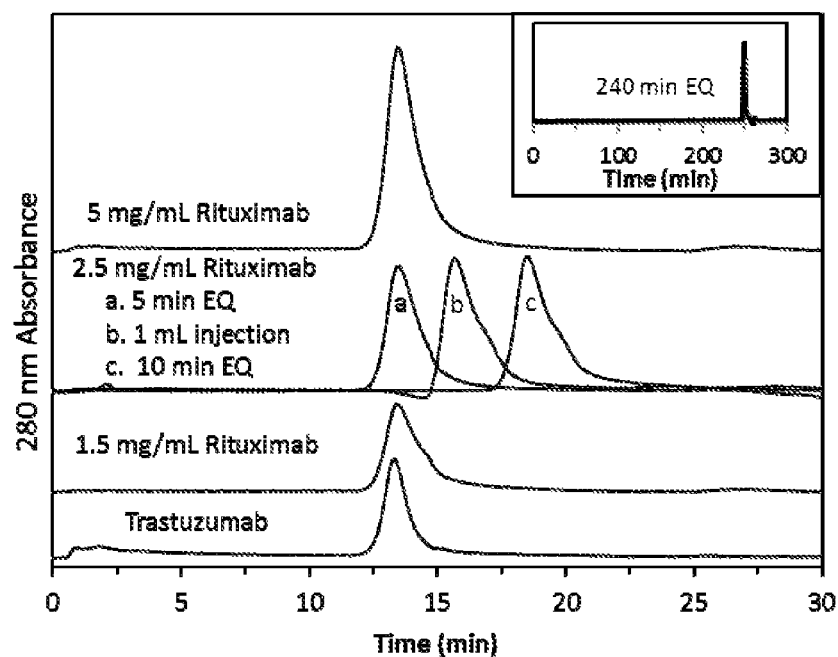
FIG. 4B is a graph displaying elution times correlated to gradient modifications, in accordance with various embodiments.

Changing the wash/bind time from 5 to 10 minutes resulted in a 4.91 minute shift of the antibody elution peak, which nearly identically matched the wash/bind time modification. In an extreme example, the wash/bind time was changed from 5 to 240 minutes, resulting in an antibody elution time change of 235.01 minutes. Thus, the antibody retention on the column may not be attributed to size exclusion effects (FIG. 4A). Varying the ELS elution gradient time resulted in only a slight change in the antibody elution time observed and resulted in peak widening. Peak integration values of the 280 nm signal are illustrated in FIG. 4B to assess capture efficiency under various injection conditions and gradient modifications.

In various embodiments, the efficiency of the platform at binding and recovering all injected antibody in solution was demonstrated by injecting Rituximab™ at different protein and initial salt concentrations. Increasing the antibody concentration and correlating it to the 280 nm elution peak integration values yielded a linear correlation, and indicated that no antibody was left bound to the column after the elution gradient was completed. The largest injection amount was 20 µL of 10 mg/mL unpurified Rituximab™ (9 mg/mL sodium chloride, 7.35 mg/mL trisodium citrate dihydrate, 0.7 mg/mL polysorbate 80, and water at pH 6.5) corresponding to 0.2 mg of antibody with a resin volume of 785 µL without observing signs of maxing out the column capacity. In various embodiments, the initial 280 nm absorbance on the chromatogram was associated with the removal of the antibody from the preservatives in the buffer it was supplied in, and did not contain an appreciable amount of antibody. This indicates that in various embodiments, the minimum binding capacity of this platform may be 0.25 mg antibody per mL of packed resin.

Figure 4C:
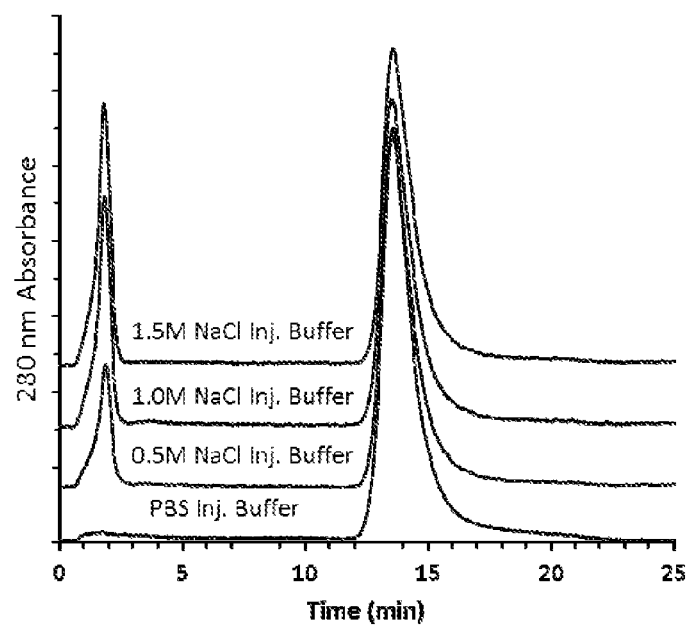
FIG. 4C is a graph illustrating the effects on antibody retention of adjusting the amount of salt content in the injection buffer, in accordance with various embodiments.

In some embodiments, the Rituximab™ was buffer exchanged to remove trisodium citrate and polysorbate 80 because they interfered with indole binding to the nucleotide binding site. In other embodiments, removal of these additives was not needed due to the avidity enhancement associated with multiple nucleotide binding site interactions with multiple indole molecules on the resin surface. In various embodiments, as the salt concentration in the crude antibody injection buffer increased, the column's efficiency in binding the antibody decreased FIG. 4C. However, this did not result in an increase of the column binding non-antibody proteins present in the crude injection. In various embodiments, salt concentrations up to PBS values resulted in little to no loss of antibody during the initial wash step. In various embodiments, diluting the sample in EQ buffer to reduce the salt and protein concentrations in solution enhanced the purification technique.

Example 6

Controls

This Example describes various controls that were used to verify that indole-3-butyric acid was solely responsible for the affinity purification of the antibody via binding to the nucleotide binding sites.

Purely Acetylated Resin

Figure 5A:
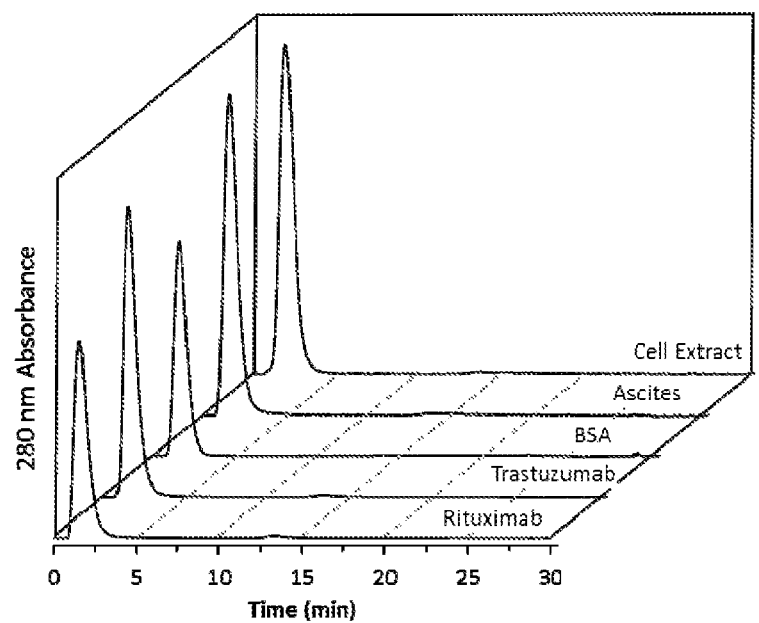
FIG. 5A is a graph illustrating an acetylated ToyoPearl AF-Amino-650M packed C1000 column chromatogram that shows nearly no nonspecific interactions between proteins and the non-indole-functionalized resin, in accordance with various embodiments.
Figure 5B:
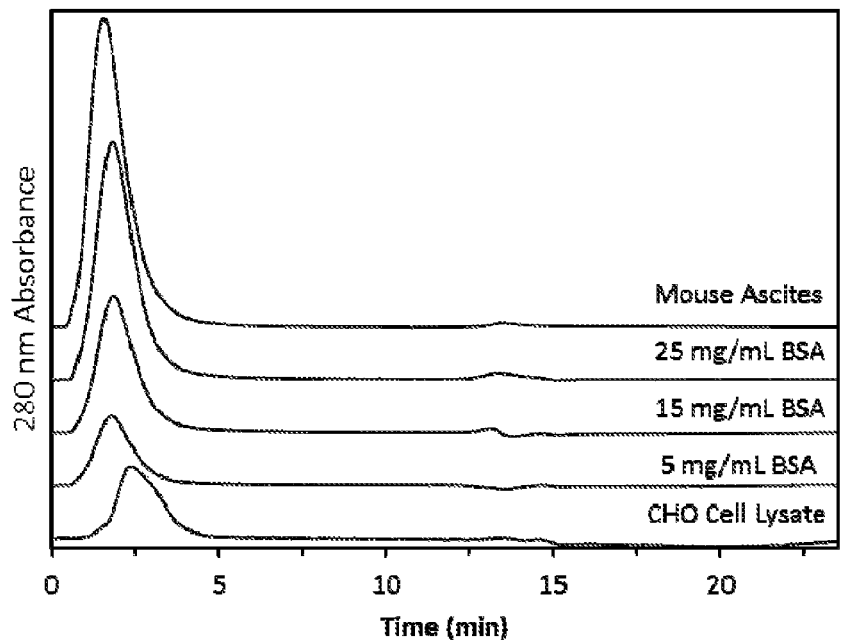
FIG. 5B is a graph illustrating limited to no nonspecific interactions between non-antibody proteins and the IBA-functionalized ToyoPearl resin, in accordance with various embodiments.

In various embodiments, acetylated ToyoPearl™ resin was synthesized by aqueous acetylation via acetic anhydride in a sodium acetate buffer and packed into a column following the protocol outlined above in Example 3. In various embodiments, this control resin was used to verify that interaction between the antibody and the resin backbone did not cause the observed separation effects. In various embodiments, the process of acetylation was used to cap the positively charged amine groups that are known to produce undesirable nonspecific protein interactions. In various embodiments, a common quantitative Kaiser test was used to verify that all the amines were acetylated. FIG. 5A is a graph illustrating an acetylated ToyoPearl AF-Amino-650M packed C1000 column chromatogram that shows nearly no nonspecific interactions between proteins and the non-indole-functionalized resin, and FIG. 5B is a graph illustrating limited to no nonspecific interactions between non-antibody proteins and the IBA-functionalized ToyoPearl resin, in accordance with various embodiments. In various embodiments, all of the samples injected on the acetylated resin eluted within the 5 minute wash/bind time. All sample injection volumes were 20 μl, and changing the injection buffer had no effect on column performance. In various embodiments, the samples included: Rituximab™, Trastuzumab (Herceptin™), bovine serum albumin (BSA), mouse ascites fluid, and cell extract. When injecting Rituximab™, a very small (<0.01% of protein) elution peak was visible that is likely associated with nonspecific protein adherence to the LC tubing or the C-1000 guard column casing, itself. This is evident because the amount of protein adsorbed was independent of the amount of Rituximab™ being injected.

Non-Modified Resin

In various embodiments, unmodified ToyoPearl™ Resin was washed with water, 0.1 N NaOH, and then water again, and was prepared as outlined above in Example 3. In various embodiments, the amine loading for the batch of resin used was 87 μmol/mL of packed resin. In various embodiments, this control resin was used to measure the elution profile for antibodies and proteins interacting with the positively charged amines on the resin surface, and to show that the separation was not merely an ion exchange phenomenon that involved preferential binding of antibody over other proteins.

In various embodiments, injecting Rituximab™ resulted in a small amount of retained antibody, with most of the antibody flowing through the column during the initial wash/bind time. In various embodiments, the retained antibody peak area was much smaller than that of the Rituximab™ injections that were fully retained on the indole-modified resin, indicating that the antibody retention was not an ion exchange phenomenon. In various embodiments, mouse ascites fluid, cell extract, and various other antibody injections resulted in peaks eluting both in the wash/bind and the elution gradient, with the dominant protein release always occurring during the initial wash/bind.

Size Exclusion Chromatography

Figure 6:
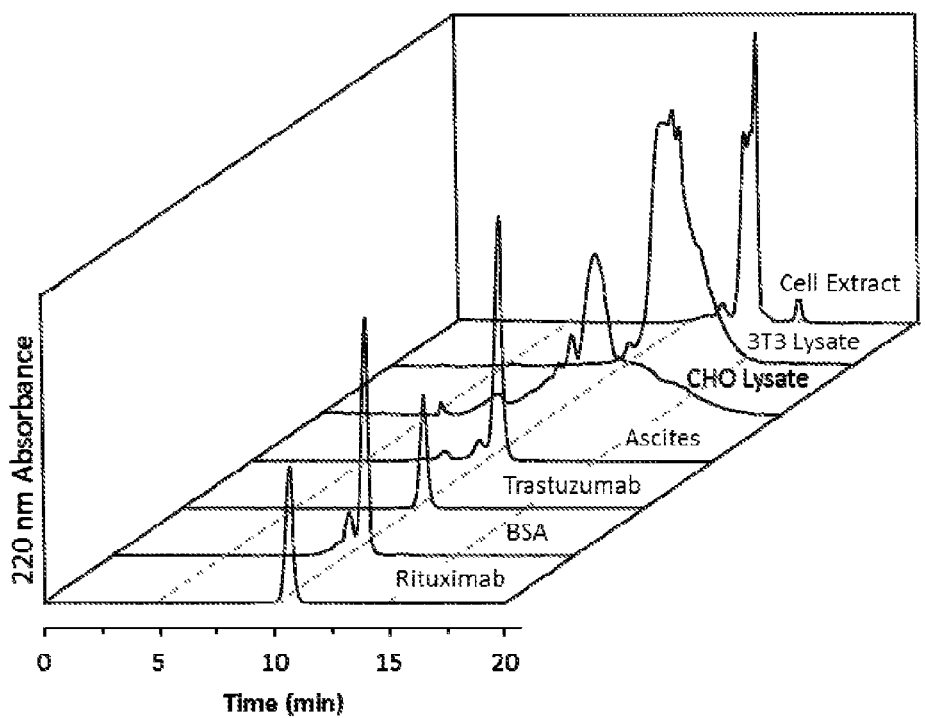
FIG. 6 is a graph showing the protein size distribution chromatograms of various cell lysate and ascites fluid samples based on a size exclusion separation by a Tosoh Biosciences TSKgel G4000SW$_{XL}$ column (larger proteins eluting before smaller), in accordance with various embodiments.

In various embodiments, a Tosoh Biosciences G4000SW$_{XL}$ size exclusion column was used to produce a globular protein size distribution of the proteins contained in Chinese hamster ovary (CHO) cell lysate, cell supernatant, and mouse ascites fluid controls. FIG. 6 is a graph showing the protein size distribution of these various cell lysate and ascites fluid samples that do not contain any immunoglobulin, in accordance with various embodiments. When performing size exclusion chromatography, proteins with a larger hydrodynamic radius elute earlier then smaller proteins with the assumption that there is minimal interaction between the resin backbone and the proteins in solution. In various embodiments, these samples were chosen as a proof of concept application for the use of small molecule affinity chromatography for the separation of pharmaceutical antibodies via the nucleotide binding site under typical industry purification conditions. Ascites fluid, conditioned cell supernatant and CHO cell lysate are very poorly characterized, complex mixtures of secreted proteins that can vary greatly in content between animal species and cell type. Reference elution times and protein molecular weights were as follows: Rituximab™ (145 kDa) had an elution time of 10.3 minutes, BSA (66 kDa) had an elution time of 10.8 minutes, and eGFP (26 kDa) had an elution time of 11.4 minutes.

Antibody Purification from a Defined Protein Mixture

Figure 7A:
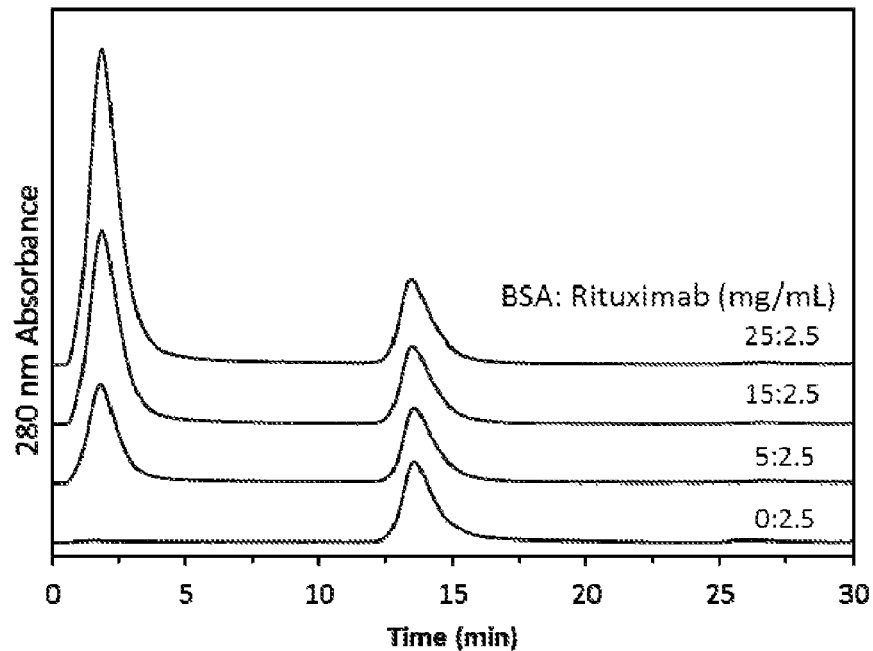
FIG. 7A is a graph showing chromatograms of injections on an indole-functionalized non-acetylated C-1000 column with EQ as the injection buffer at various bovine serum albumin (BSA) concentrations with a fixed Rituximab concentration, in accordance with various embodiments.

In various embodiments, a known amount of Rituximab™ was added into known amounts of bovine serum albumin (BSA) at various concentrations, and the antibody capture efficiency and purity were assessed. The small molecule employed for this separation was indole-3-butyric acid coupled to the ToyoPearl™ resin via the EDC aqueous coupling procedure outlined above in Example 3, with an indole loading of 58.3 μmol/mL based on a quantitative Kaiser test. Prior to injecting Rituximab-added samples, minimal interaction between the indole functionalized resin and the various protein mixtures being employed was verified. FIG. 7A is a graph showing chromatograms of injections on an indole-functionalized non-acetylated C-1000 column with EQ as the injection buffer at various bovine serum albumin (BSA) concentrations with a fixed Rituximab concentration, in accordance with various embodiments. In total, six samples were prepared and purified via the small molecule affinity chromatography technique: (1) 2.5 mg/mL Rituximab™, 5 mg/mL BSA, 20 μL injection in EQ buffer (a 1:2 Rituximab™:BSA ratio by weight, and a 1:4 ratio by number of moles); (2) 2.5 mg/mL Rituximab™, 15 mg/mL BSA, 20 μL injection in EQ buffer (a 1:6 Rituximab™:BSA ratio by weight, and a 1:12 ratio by number of moles); 2.5 mg/mL Rituximab™, 25 mg/mL BSA, 20 μL injection in EQ buffer (a 1:10 Rituximab™:BSA ratio by weight, and a 1:20 ratio by number of moles); and duplicates of the above three samples in 1M NaCl injection buffer.

Figure 7B:
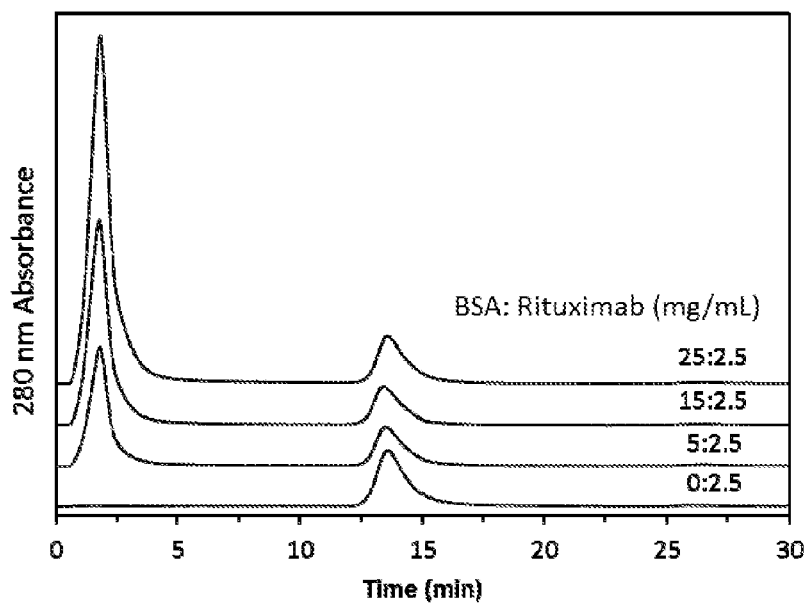
FIG. 7B is a graph showing chromatograms of injections on an indole-functionalized non-acetylated C-1000 column with 1M NaCl as the injection buffer at various BSA concentrations with a fixed Rituximab concentration, in accordance with various embodiments.
Figure 7C:
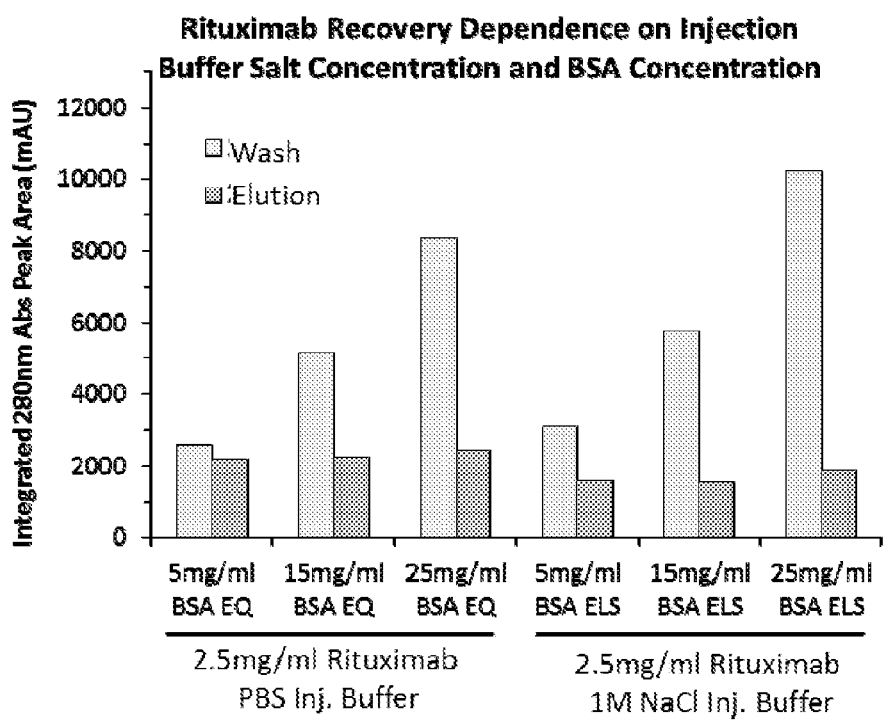
FIG. 7C is a table showing peak integrations at 280 nm and comparing the wash (0.5-4 minutes) and elution (12-15.5 minutes) peaks from the EQ and 1M NaCl injection buffer samples in FIGS. 7A and 7B respectively, in accordance with various embodiments.

In various embodiments, the samples were injected via manual injection onto the column under the specified operational conditions outlined above in Example 4. Two fractions were collected during the run with a volume of 1.75 mL each: the wash/bind fraction from 0.5-4.0 minutes, and the elution fraction from 12.0-15.5 minutes. FIG. 7B is a graph showing chromatograms of injections on an indole-functionalized non-acetylated C-1000 column with 1M NaCl as the injection buffer at various BSA concentrations with a fixed Rituximab concentration, and FIG. 7C is a table showing peak integrations at 280 nm and comparing the wash (0.5-4 minutes) and elution (12-15.5 minutes) peaks from the EQ and 1M NaCl injection buffer samples in FIGS. 7A and 7B respectively, in accordance with various embodiments. Rituximab™ eluting in the wash/bind peak was readily visible by an increase in the wash/bind peak and a decrease in the elution peak intensities for the samples containing 1M NaCl as an injection buffer. The EQ injection buffer set showed a consistent recovery of Rituximab regardless of the BSA content, as indicated by very reproducible elution peak integration values. As an initial verification of antibody recovery, the elution peak integrations were compared to an equal injection of antibody injected without BSA, and to the other two samples in the injection set, showing a consistent value in all cases.

Example 7

Verification of Separation

This Example illustrates the verification of the separation of the samples described in Example 6 using three different methods: Size Exclusion Chromatography (SEC), ELISA, and Poroshell C8 Reverse Phase HPLC (IPA).

Antibody Purity Based on SEC

Figure 8A:
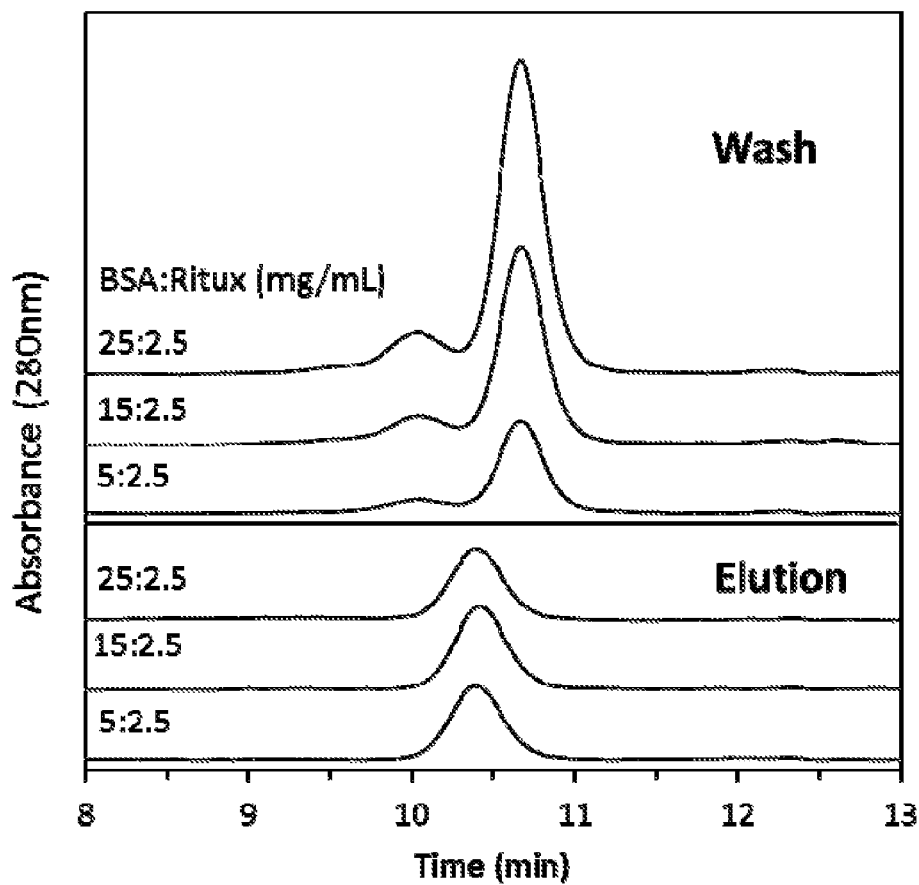
FIG. 8A illustrates size exclusion chromatography of the individual collected wash/bind and elution peaks from the small molecule antibody/BSA separations with EQ as the injection buffer (FIG. 7A), in accordance with various embodiments.
Figure 8B:
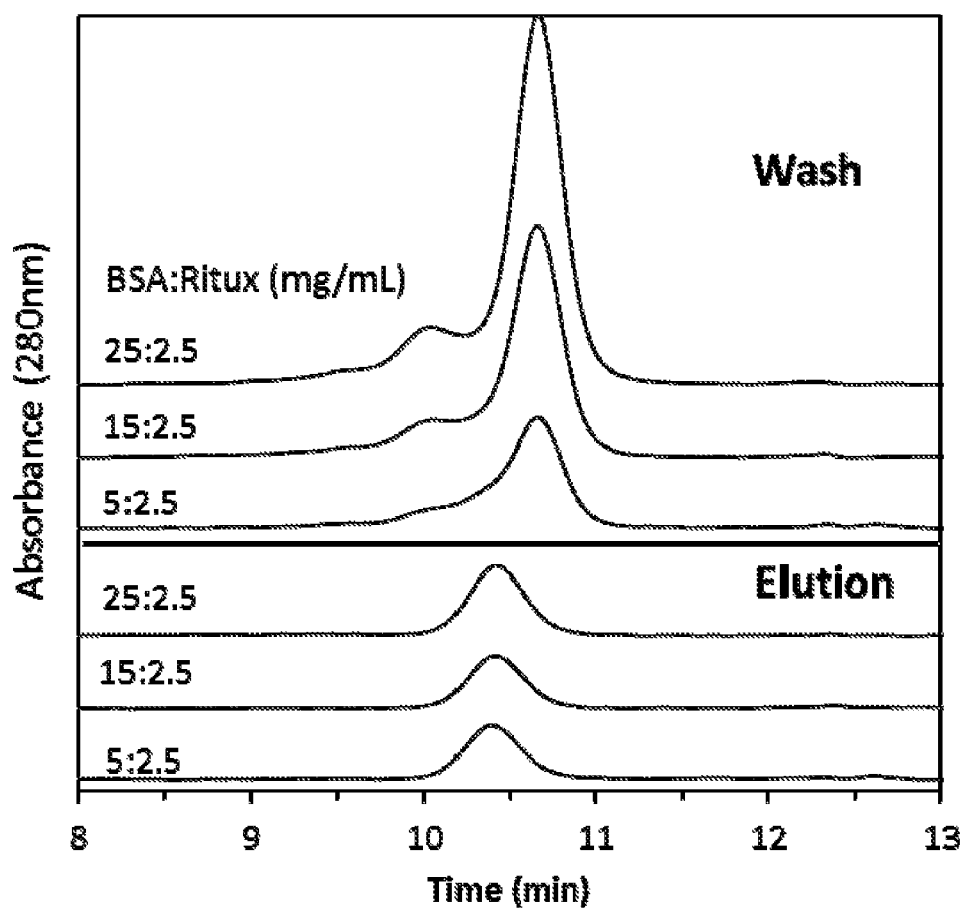
FIG. 8B illustrates size exclusion chromatography of the individual collected wash/bind and elution peaks from the small molecule antibody/BSA separations with 1M NaCl as the injection buffer (FIG. 7B), in accordance with various embodiments.

In various embodiments, to relatively quantify antibody purity from the BSA after co-injection on the small molecule affinity column as described above in Example 6, SEC was carried out on each collected fraction using a Tosoh G4000SW$_{XL}$ column. FIG. 8A illustrates size exclusion of the individual collected wash/bind and elution peaks from the small molecule antibody/BSA separations with EQ as the injection buffer, and FIG. 8B illustrates size exclusion of the individual collected wash/bind and elution peaks from the small molecule antibody/BSA separations with 1M NaCl as the injection buffer, in accordance with various embodiments. While the molecular weight difference between the Rituximab™ and BSA was nearly 80 kDa, their elution profiles on this column overlapped significantly due to nonspecific protein interactions with the column packing material, resulting in BSA eluting earlier than expected. The two peaks present in the BSA injections, at 10.0 and 10.8 min, were associated with BSA dimer and monomer, respectively. As illustrated in the EQ buffer injection sample set (FIG. 8A) there is nearly a baseline separation of the BSA dimer and monomer peaks. In the case of the 1M NaCl injection buffer sample set (FIG. 8B) the separation between BSA dimer and monomer was no longer clear, and the overall elution peak intensity was less than that of the EQ buffer sample set demonstrating the presence of antibody in the wash peak, reduced column capture efficiency. Additionally, there was no observable shouldering on any of the elution peaks, qualitatively indicating that the antibody was separated from the BSA with a high level of purity independent of column capture efficiency.

ELISA Demonstration of Column Capture Efficiency

Figure 9:
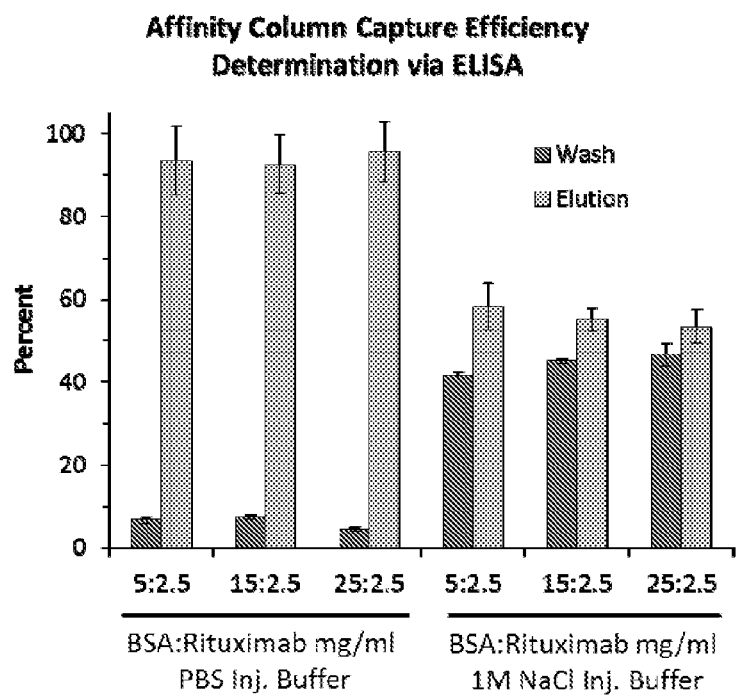
FIG. 9 is a graph showing the capture efficiency of the small molecule affinity chromatography system and the effects of high salt in the injection buffer via direct ELISA detection of the antibody in each collected fraction, in accordance with various embodiments.

In various embodiments, the samples collected from the small molecule affinity separation described above were diluted in a carbonate bicarbonate coating buffer pH 9.6 and directly adsorbed on a high binding ELISA surface to quantify the antibody content of each fraction. Successful detection of the antibody, via ELISA, also served the purpose of demonstrating that the high salt exposure did not have a permanent or significant effect on the antibodies' conformation. FIG. 9 is a graph showing the capture efficiency of the small molecule affinity chromatography system and the effects of high salt in the injection buffer via direct ELISA, in accordance with various embodiments. Even extended exposure to 2M NaCl for three weeks at 4° C. had no negative conformational effect, indicating that the antibody does not need to be collected into a secondary solution and buffer exchange post purification is not necessary. Greater than 92% capture efficiency was seen in all separations carried out with EQ buffer as the injection solvent, with the highest capture efficiency of 95.6% associated with the sample containing the greatest concentration of BSA, 25 mg/mL (FIG. 9).

The 1M NaCl injection buffer samples resulted in greatly reduced capture efficiency, illustrating the negative effects of high salt content in the injection buffer on column performance.

Poroshell C8 Reverse Phase HPLC (IPA) Antibody Purity

Figure 10A:
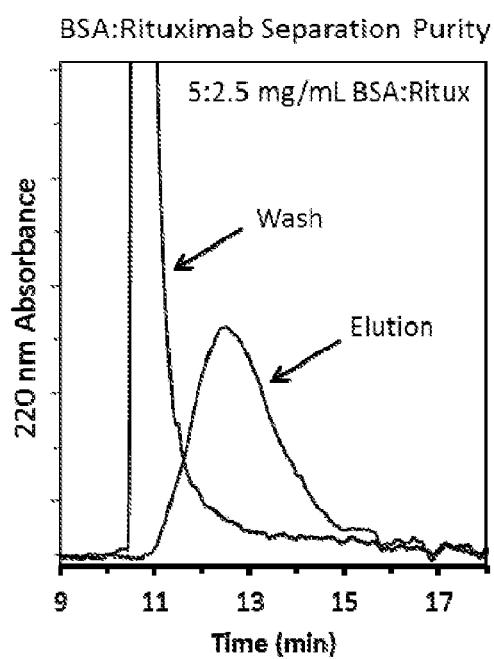
FIGS. 10A, 10B, and 10C are three graphs illustrating reverse phase high pressure liquid chromatography (RP-HPLC) of EQ injection buffer samples to assess the purity of the antibody post small molecule affinity chromatography and the separation efficiency of three BSA:Rituximab™ contamination ratios: 5:2.5 mg/mL (FIG. 10A), 15:2.5 mg/mL (FIG. 10B), and 25:2.5 mg/mL (FIG. 10C), in accordance with various embodiments.
Figure 10B:
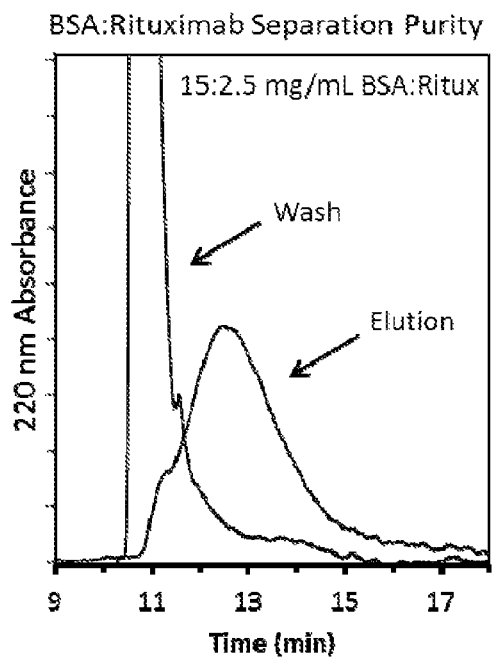
Figure 10C:
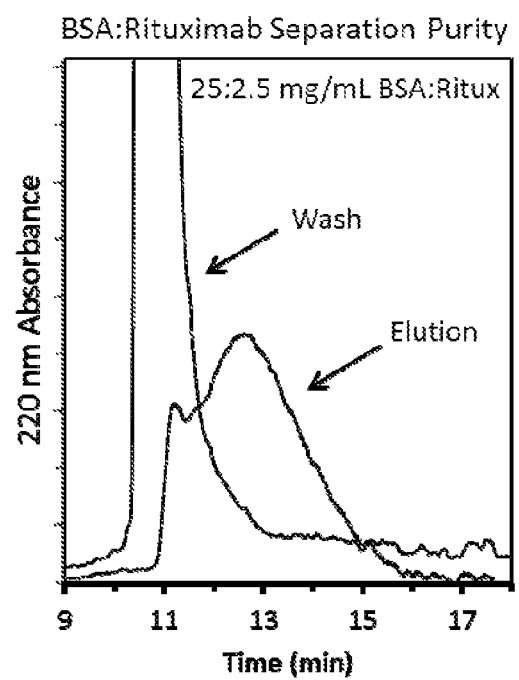

To assess the antibody purity, reverse phase high pressure liquid chromatography (RP-HPLC) was employed using isopropyl alcohol as the organic phase. FIGS. 10A, 10B, and 10C are three graphs illustrating reverse phase high pressure liquid chromatography (RP-HPLC) of EQ injection buffer samples to assess the purity of the antibody post small molecule affinity chromatography and the separation efficiency of three BSA:Rituximab™ contamination ratios: 5:2.5 mg/mL (FIG. 10A), 15:2.5 mg/mL (FIG. 10B), and 25:2.5 mg/mL (FIG. 10C), in accordance with various embodiments. Turning to FIG. 10A, no shoulder was present on the 5 mg/mL BSA/Rituximab™ separation, signifying a negligible amount of BSA in the elution peak and a nearly 100% pure antibody. As shown in FIGS. 10B and 10C, In the 15 and 25 mg/mL BSA/Rituximab™ separations, a shoulder was evident in the elution peak, indicating some BSA contamination in the purified antibody product. Using Origin 7, these elution profiles were fit with a Gaussian function, and the remaining shoulders were integrated to accurately quantify the exact amount of BSA contamination. The resulting antibody purities from this analysis were: 100%, 98.4%, and 93.2% pure antibody in the elution peak, with BSA removal efficiencies of 100%, 99.64% and 98.98% for 5 mg/mL, 15 mg/mL, and 25 mg/mL BSA separation concentrations, respectively. Only the EQ injection buffer samples were analyzed by this technique. By increasing the EQ wash time at the start of the injection cycle, the amount of non-antibody contamination present in the elution peak was reduced, and in many cases eliminated, to provide for a more pure antibody product (data not shown).

Matrix Assisted Laser Desorption Ionization Time of Flight Mass Spectrometry (MALDI-TOFMS)

Figure 11A:
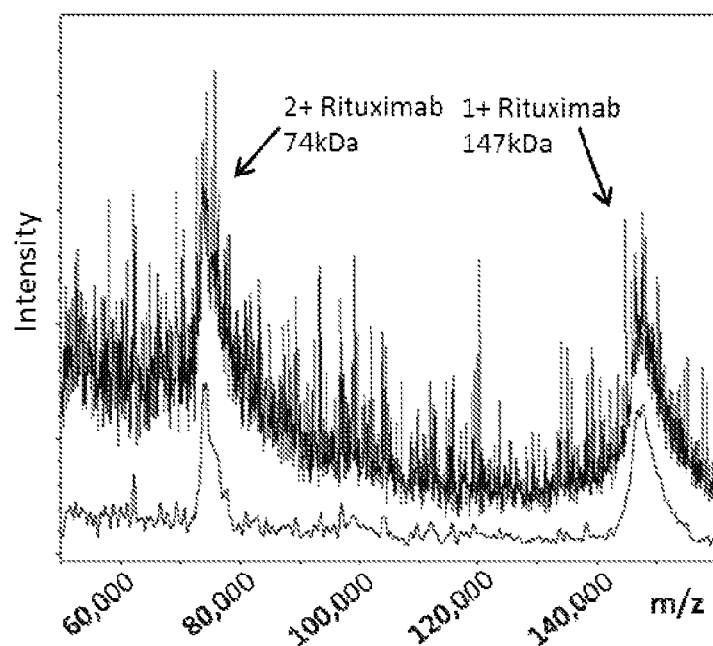
FIG. 11A is a graph illustrating MALDI-TOF MS carried out on the 25 mg/mL BSA, 2.5 mg/mL Rituximab™ separation data, showing the raw and smoothed data of the elution fraction, in accordance with various embodiments.
Figure 11B:
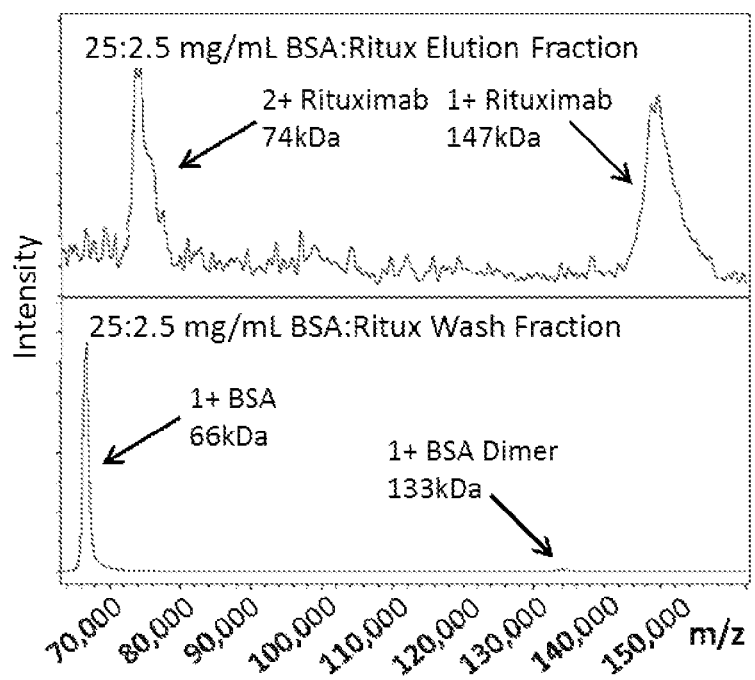
FIG. 11B is a graph illustrating MALDI-TOF MS carried out on the 25 mg/mL BSA, 2.5 mg/mL Rituximab™ separation data with EQ as the injection buffer, showing that the elution fraction contained only doubly (74 kDa) and singly (148 kDa) charged Rituximab™ and the wash/bind fraction showed monomer BSA singly charged (66 kDa), as well as singly charged BSA dimer (133 kDa), in accordance with various embodiments.
Figure 11C:
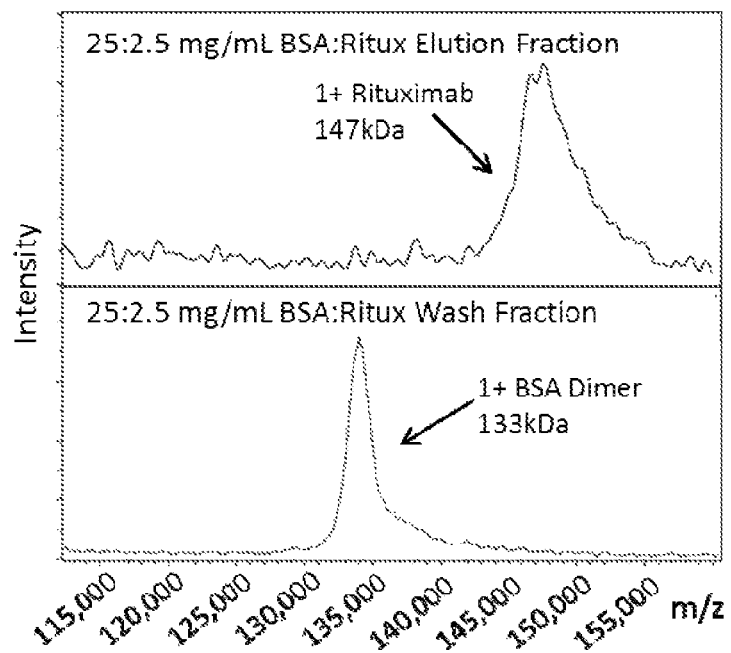
FIG. 11C is a graph illustrating MALDI-TOF MS carried out on the 25 mg/mL BSA, 2.5 mg/mL Rituximab™ separation data, showing a stacked mass spectrum comparison of singly charged BSA dimer and singly charged Rituximab™, in accordance with various embodiments.

To further characterize the elution peak purity, mass spectrometry was carried out on both collected fractions from the 2.5 mg/mL Rituximab™, 25 mg/mL BSA separation. Samples were spotted on a stainless steel target with sinapic acid as a matrix and analyzed on a Bruker Autoflex III MALDI-TOFMS. FIG. 11A is a graph illustrating MALDI-TOF MS carried out on the 25 mg/mL BSA, 2.5 mg/mL Rituximab™ separation data, showing that the elution fraction showed only doubly (74 kDa) and singly (148 kDa) charged Rituximab™, FIG. 11B is a stacked mass spectrum illustrating MALDI-TOF MS carried out on the 25 mg/mL BSA, 2.5 mg/mL Rituximab™ separation data, showing that the elution fraction with doubly (74 kDa) and singly (148 kDa) charged Rituximab™ and the wash/bind fraction showed monomer BSA singly charged (66 kDa) as well as singly charged BSA dimer (133 kDa), and FIG. 11C is a graph illustrating MALDI-TOF MS carried out on the 25 mg/mL BSA, 2.5 mg/mL Rituximab™ separation data, showing a stacked mass spectrum comparison of singly charged BSA dimer and singly charged Rituximab™, in accordance with various embodiments. The small amount of antibody present in the wash/bind fraction was not visible on the wash/bind fraction mass spectrum due to ion suppression by the much larger amount of BSA in the sample. Based on the RP-HPLC data above, it was expected that a BSA peak would be visible in the elution fraction, since 6.8% of the sample, based on peak area integration at 220 nm, is BSA. However, there is no BSA peak visible, which indicates that the purity based on RP-HPLC is an underestimate, and the antibody sample purity is likely greater than 93.2%.

Figure 12:
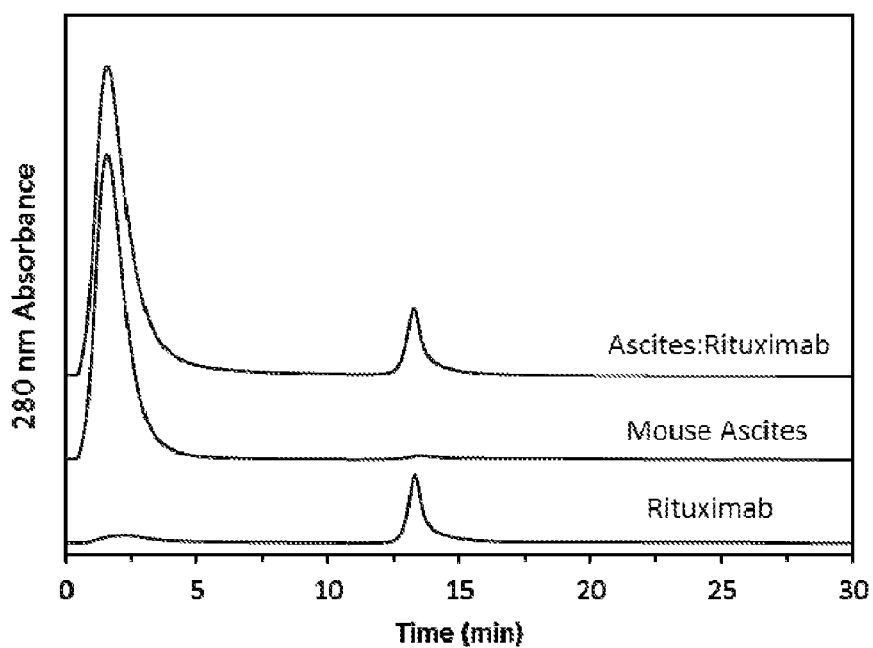
FIG. 12 is a graph illustrating the separation of Rituximab and added mouse ascites fluid on an indole-functionalized ToyoPearl resin, as well as the elution profiles of the Rituximab and mouse ascites when injected separately, in accordance with various embodiments.

To demonstrate the use of small molecule affinity chromatography to purify antibodies from biological samples, Rituximab was added into an immunoglobulin free mouse ascites fluid. FIG. 12 is a graph illustrating the separation of Rituximab-added mouse ascites fluid on an indole-functionalized ToyoPearl resin. Also displayed are the elution profiles of the Rituximab and mouse ascites when injected separately. Based on 280 nm absorbance peak integrations, approximately 97% of the Rituximab injected was recovered in the elution peak.

In various embodiments, the production of pharmaceutical antibodies in industry may be carried out in very large bioreactors using immortalized antibody secreting cell lines. In these embodiments, the first step in the antibody purification process may include removing the cells from the bioreactor fluid, which is often accomplished by membrane filtration. In embodiments, the cell free supernatant may then be processed via serial methods of purification to separate the antibody content from various other residual cell components. In one example, to demonstrate the use of small molecule affinity chromatography for pharmaceutical antibody purification, Rituximab was added into four different cell conditioned supernatants in three different media preparations, which were then separated on an indole-functionalized ToyoPearl™ small molecule affinity resin.

The cell lines and media conditions were as follows: SKOV3 Ovarian cancer adherent cell line (DMEM with 10% FBS), BT474 (M1 variant) tumorigenic adherent breast cancer cell line (RPMI with 10% FBS), SKBR3 Breast cancer adherent cell line (McCoys with 10% FBS), H929 Multiple myeloma suspension cancer cell line (RPMI with 20% FBS, 0.01% β-mercaptoethanol). The adherent cell lines were split and plated at approximately 50% confluence. The media was allowed to be conditioned for 3 days (90% confluence) prior to removal and centrifugation at 8,000 RCF for 3 minutes. The suspension cell line was split and allowed to grow for 3 days to condition the media with a final cell density of 1 million cells/mL and was subsequently centrifuged to remove whole cell content.

Figure 13A:
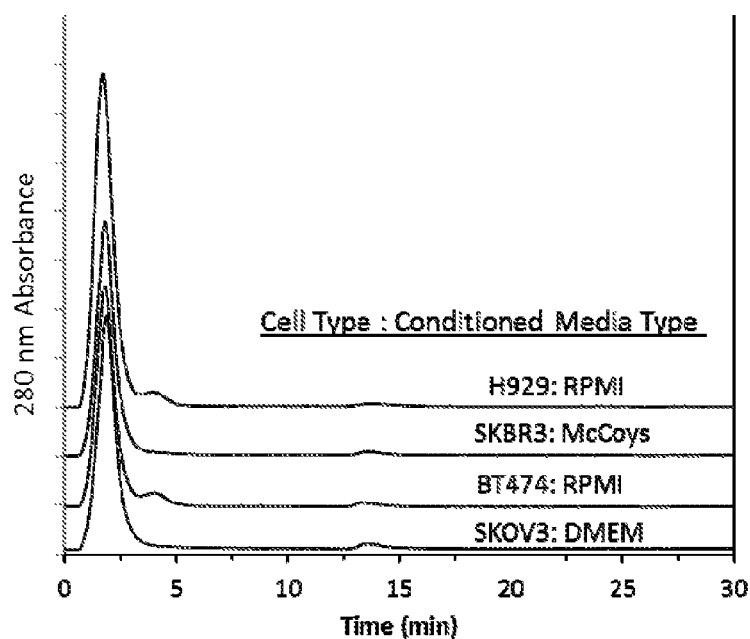
FIG. 13A is a stacked graph illustrating injection of four different cell conditioned media preparations on an indole-functionalized ToyoPearl column displaying minimal non-specific protein interacting with the column, in accordance with various embodiments.
Figure 13B:
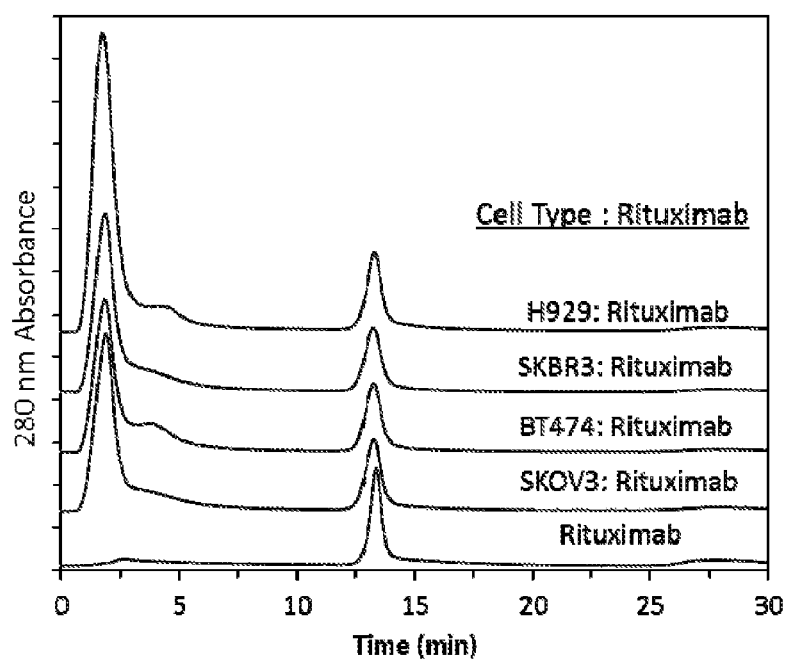
FIG. 13B is a stacked graph illustrating Rituximab purifications from conditioned cell supernatant on an indole-functionalized ToyoPearl column displaying consistent Rituximab recovery from the samples, in accordance with various embodiments.

FIG. 13A is a stacked graph illustrating injection of the four different cell conditioned media preparations on an indole-functionalized ToyoPearl™ column displaying minimal non-specific protein interacting with the column. This also serves the purpose to demonstrate the very low level of immunoglobulin present in the FBS, approximately 0.01 mg/mL. The cell conditioned media was then added with Rituximab at 1 mg/mL and was subsequently purified on the small molecule affinity purification column. FIG. 13B is a stacked graph illustrating Rituximab purifications from conditioned cell supernatant on an indole-functionalized ToyoPearl column displaying consistent Rituximab recovery from the samples. Based on 220 nm absorbance integrations of the elution peaks there is greater than 92% antibody capture efficiency in all four of the cell supernatant separations.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

---

What is claimed is:

1. A method of binding an immunoglobulin, comprising:
providing a small molecule that specifically binds a nucleotide binding site on an immunoglobulin;
contacting a composition containing an immunoglobulin with the small molecule under conditions suitable for binding of the immunoglobulin to the small molecule; and
separating the small molecule from the composition, wherein the immunoglobulin remains bound to the small molecule:
wherein the small molecule is indole 3-butyric acid; and
wherein the small molecule has a monovalent $K_d$ of about 150 μM or less for a nucleotide binding site defined as:
A. phenylalamine 35 of SEQ. ID NO: 1;
   tyrosine 86 of SEQ. ID NO: 1;
   tyrosine 36 of SEQ. ID. NO: 2: and
   tyrosine 87 of SEQ. ID. NO: 2; or
B. tyrosine 95 of SEQ. ID NO: 3;
   tryptophan 111 of SEQ. ID NO: 3;
   tyrosine 95 of SEQ. ID. NO: 4; and
   tryptophan 110 of SEQ. ID. NO: 4.

2. The method of claim 1, wherein the small molecule is coupled to a solid support, and wherein separating the small molecule from the composition comprises separating the solid support from the composition.

3. The method of claim 2, wherein separating the small molecule from the composition comprises washing the solid support.

4. The method of claim 2, wherein the solid support comprises a resin, a bead, a particle, a membrane, a capillary, a microarray, a surface or a multiple well plate.

5. The method of claim 4, wherein the solid support comprises a resin, and wherein the resin is utilized as a slurry.

6. The method of claim 4, wherein the solid support comprises a resin, and wherein the resin is packed in a chromatography column.

7. The method of claim 6, wherein the small molecule is coupled to the resin via an amide bond.

8. The method of claim 6, wherein contacting the composition containing an immunoglobulin with the small molecule comprises applying a mobile phase comprising the composition to the chromatography column.

9. The method of claim 8, wherein separating the small molecule from the composition comprises applying an elution buffer to the chromatography column.

10. The method of claim 2, wherein contacting the composition containing an immunoglobulin with the small molecule comprises contacting the solid support with a mobile phase comprising the composition.

11. The method of claim 1, further comprising a step of causing the small molecule to release the immunoglobulin.

12. The method of claim 1, wherein the composition comprises ascites fluid, cell supernatant, or cell lysate.

13. The method of claim 1, wherein the immunoglobulin is a monoclonal antibody, a polyclonal antibody, or a mixture thereof.

14. A method of purifying an antibody, comprising:
providing a small molecule that specifically binds a nucleotide binding site on an immunoglobulin, wherein the small molecule is an aromatic planar compound coupled to a resin;
contacting the small molecule with a mobile phase comprising the antibody under conditions suitable for binding of the antibody to the small molecule;
washing the resin to remove the mobile phase, wherein the antibody remains bound to the small molecule; and
applying an elution buffer to the resin, thereby eluting the purified antibody from the resin;
wherein the small molecule has a monovalent $K_d$ of about 150 μM or less for a nucleotide binding site defined as:
A phenylalamine 35 of SEQ. ID NO: 1;
   tyrosine 86 of SEQ. ID NO: 1;
   tyrosine 36 of SEQ. ID. NO: 2; and
   tyrosine 87 of SEQ. ID. NO: 2; or
B. tyrosine 95 of SEQ. ID NO: 3;
   tryptophan 111 of SEQ. ID NO: 3;
   tyrosine 95 of SEQ. ID. NO: 4; and
   tryptophan 110 of SEQ. ID. NO: 4; and
wherein the small molecule is indole 3-butyric acid.

15. The method of claim 14, further comprising causing the small molecule to release the immunoglobulin.

16. The method of claim 14, wherein the resin is packed in a chromatography column.

17. The method of claim 14, wherein the resin is utilized as a slurry.

18. The method of claim 14, wherein the small molecule is coupled to the resin via an amide bond.

* * * * *

SEQUENCE LISTING

```
<160> NUMBER OF SEQ ID NOS: 4

<210> SEQ ID NO 1
<211> LENGTH: 213
<212> TYPE: PRT
<213> ORGANISM: Homo sapiens

<400> SEQUENCE: 1

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

Cys Glu Val Thr His Gln Gly Leu Ser Ser Pro Val Thr Lys Ser Phe
            195                 200                 205

Asn Arg Gly Glu Cys
    210

<210> SEQ ID NO 2
<211> LENGTH: 224
<212> TYPE: PRT
<213> ORGANISM: Homo sapiens

<400> SEQUENCE: 2

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 3
<211> LENGTH: 214
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 4
<211> LENGTH: 220
<212> TYPE: PRT
<213> ORGANISM: Homo sapiens

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro
    210                 215                 220
```